(12) United States Patent
Katz

(10) Patent No.: US 12,220,412 B2
(45) Date of Patent: Feb. 11, 2025

(54) METHODS FOR ADMINISTERING CORTICOSTEROIDS

(71) Applicant: Sparrow Pharmaceuticals, Inc., Portland, OR (US)

(72) Inventor: David A. Katz, Portland, OR (US)

(73) Assignee: Sparrow Pharmaceuticals, Inc., Portland, OR (US)

( * ) Notice: Subject to any disclaimer, the term of this patent is extended or adjusted under 35 U.S.C. 154(b) by 774 days.

(21) Appl. No.: 17/289,516

(22) PCT Filed: Aug. 14, 2019

(86) PCT No.: PCT/US2019/046449
§ 371 (c)(1),
(2) Date: Apr. 28, 2021

(87) PCT Pub. No.: WO2020/106337
PCT Pub. Date: May 28, 2020

(65) Prior Publication Data
US 2021/0393622 A1     Dec. 23, 2021

Related U.S. Application Data

(60) Provisional application No. 62/769,932, filed on Nov. 20, 2018.

(51) Int. Cl.
*A61K 31/496* (2006.01)
*A61K 31/4196* (2006.01)
(Continued)

(52) U.S. Cl.
CPC ........ *A61K 31/496* (2013.01); *A61K 31/4196* (2013.01); *A61K 31/573* (2013.01); *A61P 39/00* (2018.01)

(58) Field of Classification Search
CPC .............. A61K 31/496; A61K 31/4196; A61K 31/573; A61P 39/00
See application file for complete search history.

(56) References Cited

U.S. PATENT DOCUMENTS

| | | |
|---|---|---|
| 3,907,821 A | 9/1975 | Gall |
| 4,577,020 A | 3/1986 | Gall |
| (Continued) | | |

FOREIGN PATENT DOCUMENTS

| | | |
|---|---|---|
| CA | 2580409 | 3/2006 |
| CN | 1909902 | 2/2007 |
| (Continued) | | |

OTHER PUBLICATIONS

Kiso et al. (2018) Analgesic effects of ASP3662, a novel 11β-hydroxysteroid dehydrogenase 1 inhibitor, in rat models of neuropathic and dysfunctional pain. British Journal of Pharmacology, 175: 3784-3796. (Year: 2018).*

(Continued)

*Primary Examiner* — Matthew P Coughlin
*Assistant Examiner* — Ashli Ariana Chicks
(74) *Attorney, Agent, or Firm* — Global Patent Group Inc.; Lauren L. Stevens; Erik Larsen

(57) ABSTRACT

Provided is a method for administering a corticosteroid to a patient in need thereof, comprising: determining a target threshold for the ratio of urinary (tetrahydrocortisol+allotetrahydrocortisol) to urinary tetrahydrocortisone for the patient; and administering an HSD1 inhibitor to the patient. Also provided is a method for reducing or preventing the side effects associated with corticosteroid administration to a patient in need thereof, comprising: determining a target threshold for the ratio of urinary (tetrahydrocortisol+allotetrahydrocortisol) to urinary tetrahydrocortisone for the patient; and administering an HSD1 inhibitor to the patient.

20 Claims, 10 Drawing Sheets

(51) Int. Cl.
  *A61K 31/573*    (2006.01)
  *A61P 39/00*    (2006.01)

(56) References Cited

U.S. PATENT DOCUMENTS

| | | | |
|---|---|---|---|
| 5,045,556 | A | 9/1991 | Allgeier |
| 5,098,922 | A | 3/1992 | Allgeier |
| 7,737,137 | B2 | 6/2010 | Brune |
| 8,377,923 | B2 | 2/2013 | Yoshimura |
| 8,871,208 | B2 | 10/2014 | Jacobson |
| 9,765,040 | B2 | 9/2017 | Kiso |
| 10,648,506 | B2 | 5/2020 | Mendoza |
| 10,894,054 | B2 | 1/2021 | Pruzanski |
| 2004/0067222 | A1 | 4/2004 | Walker |
| 2004/0133011 | A1 | 7/2004 | Waddell |
| 2005/0277647 | A1 | 12/2005 | Link |
| 2006/0094699 | A1 | 5/2006 | Kampen |
| 2007/0224298 | A1 | 9/2007 | Talbott |
| 2007/0259854 | A1 | 11/2007 | Murakami |
| 2009/0082367 | A1 | 3/2009 | Yoshimura |
| 2011/0159005 | A1 | 6/2011 | Jacobson |
| 2013/0022677 | A1 | 1/2013 | Mullen |
| 2013/0338169 | A1 | 12/2013 | Bitner |
| 2017/0327474 | A1 | 11/2017 | Kiso |
| 2018/0010635 | A1 | 1/2018 | Mendoza |
| 2021/0137912 | A1 | 5/2021 | Tiganescu |
| 2023/0364060 | A1 | 11/2023 | Katz |

FOREIGN PATENT DOCUMENTS

| | | | | |
|---|---|---|---|---|
| CN | 101014578 | | 8/2007 | |
| CN | 101198605 | A | 6/2008 | |
| EP | 1790641 | | 5/2007 | |
| EP | 1798226 | | 6/2007 | |
| EP | 1995243 | | 11/2008 | |
| EP | 2298747 | | 3/2011 | |
| JP | 2005170939 | | 6/2005 | |
| JP | 2007515484 | | 6/2007 | |
| TW | 201006804 | | 2/2010 | |
| WO | 2002076435 | | 10/2002 | |
| WO | 2003040110 | | 5/2003 | |
| WO | 2003059267 | | 7/2003 | |
| WO | 2003065983 | | 8/2003 | |
| WO | 2003104207 | | 12/2003 | |
| WO | 2003104208 | | 12/2003 | |
| WO | 2004014881 | | 2/2004 | |
| WO | 2004089367 | | 10/2004 | |
| WO | 2004089380 | | 10/2004 | |
| WO | 2004089470 | | 10/2004 | |
| WO | 2004106294 | | 12/2004 | |
| WO | 2005044192 | | 5/2005 | |
| WO | 2005060963 | | 7/2005 | |
| WO | 2005065683 | | 7/2005 | |
| WO | 2005097759 | | 10/2005 | |
| WO | 2006013948 | | 2/2006 | |
| WO | 2006030805 | | 3/2006 | |
| WO | 2006048750 | | 5/2006 | |
| WO | 2006068199 | | 6/2006 | |
| WO | 2006080533 | | 8/2006 | |
| WO | 2006134467 | | 12/2006 | |
| WO | 2006134481 | | 12/2006 | |
| WO | 2007007688 | | 1/2007 | |
| WO | 2007021941 | | 2/2007 | |
| WO | 2007040982 | | 4/2007 | |
| WO | 2007105753 | | 9/2007 | |
| WO | 2010001946 | | 1/2010 | |
| WO | 2010121814 | | 10/2010 | |
| WO | 2011068927 | | 6/2011 | |
| WO | WO-2011068927 | A2 * | 6/2011 | ............ A61K 31/00 |
| WO | 2012033070 | | 3/2012 | |
| WO | 2018117063 | | 6/2018 | |
| WO | 2020106337 | | 5/2020 | |
| WO | 2021180643 | | 9/2021 | |
| WO | 2023225507 | | 11/2023 | |

OTHER PUBLICATIONS

Tomlinson et al. Inhibition of 11beta-hydroxysteroid dehydrogenase type 1 activity in vivo limits glucocorticoid exposure to human adipose tissue and decreases lipolysis. J Clin Endocrinol Metab. 2007;92(3):857-864. (Year: 2007).*

Nicolaides et al. Glucocorticoid Therapy and Adrenal Suppression. [Updated Oct. 19, 2018]. In: Feingold KR, Anawalt B, Blackman MR, et al., editors. Endotext [Internet]. South Dartmouth (MA): MDText.com, Inc.; 2000-. Accessed Apr. 3, 2024 from https://www.ncbi.nlm.nih.gov/books/NBK279156/. (Year: 2018).*

Allende F et al., LC-MS/MS Method for the Simultaneous Determination of Free Urinary Steroids, Chromatographia. 2014;77:637-642.

International Application No. PCT/US2019/046449; International Preliminary Report on Patentability, date of issuance Jun. 3, 2021; 7 pages.

International Application No. PCT/US2019/046449; International Search Report and Written Opinion of the International Searching Authority, date of mailing Oct. 24, 2019; 9 pages.

An, G. et al., "Population Pharmacokinetics of the 11β-hydroxysteroid Dehydrogenase Type 1 Inhibitor ABT-384 in Healthy Volunteers Following Single and Multiple Dose Regimens", Biopharm Drug Dispos., 35(7):417-429, (2014).

Carroll, B. et al., "A Specific Laboratory Test for the Diagnosis of Melancholia", Arch Gen Psychiatry, 38(1):15-22, (1981).

CN Patent Application No. 200980125940.0; Office Action, dated Jul. 17, 2012; 6 pages.

Csernansky, J. et al., "Plasma Cortisol and Progression of Dementia in Subjects with Alzheimer-Type Dementia", Am J Psychiatry, 163(12):2164-2169, (2006).

Davani, B et al., "Type 1 11β-hydroxysteroid Dehydrogenase Mediates Glucocorticoid Activation and Insulin Release in Pancreatic Islets", J Biol Chem., 275(45):34841-34844, (2000).

EP Patent Application No. 05783391.5; Extended European Search Report, dated Jul. 24, 2009; 9 pages.

EP Patent Application No. 07738519.3; Extended European Search Report, dated Jun. 24, 2009; 6 pages.

EP Patent Application No. 09773524.5; Extended European Search Report, dated May 15, 2012; pages.

Erhardt, A. et al., "Regulation of the Hypothalamic-Pituitary-Adrenocortical System in Patients with Panic Disorder", Neuropsychopharmacology, 31(11):2515-2522, (2006).

Erkut, Z. et al., "Stress of Dying is not Suppressed by High-dose Morphine or by Dementia", Neuropsychopharmacology, 29(1):152-157, (2004).

Holman, A. et al., "A Randomized, Double-Blind, Placebo-Controlled Trial of Pramipexole, a Dopamine Agonist, in Patients with Fibromyalgia Receiving Concomitant Medications", Arthritis & Rheumatism, 52(8):2495-2505, (2005).

Hong, H. et al., "Hypothalamic-Pituitary-Adrenal Reactivity in Boys with Attention Deficit Hyperactivity Disorder", Yonsei Med J., 44(4):608-614, (2003).

International Application No. PCT/JP2009/062081; International Preliminary Report on Patentability, date of issuance Jan. 5, 2011; 07 pages.

International Application No. PCT/JP2009/062081; International Search Report and Written Opinion of the International Searching Authority, date of mailing Sep. 1, 2009; 11 pages.

International Application No. PCT/JP2011/070205; International Search and Written Opinion of the International Searching Authority (English translation), date of mailing Nov. 15, 2011, pages.

International Application No. PCT/US2023/067057; International Search Report and Written Opinion of the International Searching Authority, date of mailing Oct. 11, 2023; 13 pages.

Katritzky, A. et al., "Ring and Side Chain Reactivities of 1-([1,3,4]oxadiazol-2-ylmethyl)-1 H-benzotriazole", ARKIVOC (ii), pp. 101-108, (2001).

Katz, D. et al., "Peripheral and Central Nervous System Inhibition of 11β-hydroxysteroid Dehydrogenase Type 1 in Man by the Novel Inhibitor ABT-384", Transl Psychiatry, 3(8):e295, 7 pages, (2013).

(56) References Cited

OTHER PUBLICATIONS

Kiso, T. et al., "Analgesic Effects of ASP3662, a Novel 11β-hydroxysteroid Dehydrogenase 1 Inhibitor, in Rat Models of Neuropathic and Dysfunctional Pain", Br J Pharmacol., 175(19):3784-3796, (2018).
Lindsay, R. et al., "Subcutaneous Adipose 11β-hydroxysteroid Dehydrogenase Type 1 Activity and Messenger Ribonucleic Acid Levels are Associated with Adiposity and Insulinemia in Pima Indians and Caucasians", J Clin Endocrinol Metab., 88(6):2738-2744, (2003).
Masuzaki, H. et al., "A Transgenic Model of Visceral Obesity and the Metabolic Syndrome", Science, 294:2166-2170, (2001).
Masuzaki, H. et al., "Transgenic Amplification of Glucocorticoid Action in Adipose Tissue Causes High Blood Pressure in Mice", J Clin Invest., 112(1):83-90, (2003).
Mease, P. et al., "A Randomized, Double-Blind, Placebo-Controlled, Phase III Trial of Pregabalin in the Treatment of Patients with Fibromyalgia", J Rheumatol, 35(3):502-514, (2008).
Morton, N. et al., "Improved Lipid and Lipoprotein Profile, Hepatic Insulin Sensitivity, and Glucose Tolerance in 11β-Hydroxysteroid Dehydrogenase Type 1 Null Mice", J Biol Chem., 276(44):41293-41300, (2001).
Pappagallo, M. "Newer Antiepileptic Drugs: Possible Uses in the Treatment of Neuropathic Pain and Migraine", Clinical Therapeutics, 25(10):2506-2538, (2003).
Patani, G. et al., "Bioisosterism: A Rational Approach in Drug Design", Chem Rev., 96(8):3147-3176, (1996).
Rask, E. et al., "Tissue-Specific Dysregulation of Cortisol Metabolism in Human Obesity", J Clin Endocrinol Metab., 86(3):1418-1421, (2001).
Rauz, S. et al., "Expression and Putative Role of 11β-Hydroxysteroid Dehydrogenase Isozymes within the Human Eye", Invest Ophthalmol Vis Sci., 42(9):2037-2042, (2001).
Russell, I. et al., "Efficacy and Safety of Duloxetine for Treatment of Fibromyalgia in Patients with or without Major Depressive Disorder: Results from a 6-month, Randomized, Double-blind, Placebo-controlled, Fixed-dose Trial", Pain, 136(3):432-444, (2008).
Sandeep, T. et al., "11β-Hydroxysteroid Dehydrogenase Inhibition Improves Cognitive Function in Healthy Elderly Men and Type 2 Diabetics", PNAS, 101(17):6734-6739, (2004).
Sindrup, S. et al., "Antidepressants in the Treatment of Neuropathic Pain", Basic & Clinical Pharmacology & Toxicology, 96(6):399-409, (2005).
Skaer, T. "Fibromyalgia: Disease Synopsis, Medication Cost Effectiveness and Economic Burden", PharmacoEconomics, 32:457-466, (2014).
U.S. Appl. No. 15/664,733; Final Office Action dated Oct. 11, 2018; 18 pages.
U.S. Appl. No. 11/663,089; Non-Final Office Action, dated Apr. 16, 2009; pages.
U.S. Appl. No. 11/663,089; Notice of Allowance, dated Apr. 6, 2010; pages.
U.S. Appl. No. 12/293,214; Non-Final Office Action, dated Nov. 23, 2009; pages.
Veen, G. et al., "Salivary Cortisol, Serum Lipids, and Adiposity in Patients with Depressive and Anxiety Disorders", Metabolism, 58(6):821-827, (2009).
Wolfe, F. et al., "The American College of Rheumatology 1990 Criteria for the Classification of Fibromyalgia", Arthritis and Rheumatism, 33(2):160-172, (1990).
Woolf, C. et al., "Neuropathic Pain: Aetiology, Symptoms, Mechanisms, and Management", Lancet, 353(9168):1959-1964, (1999).
Yau, J. et al., "Lack of Tissue Glucocorticoid Reactivation in 11β-hydroxysteroid Dehydrogenase Type 1 Knockout Mice Ameliorates Age-Related Learning Impairments", PNAS, 98(8):4716-4721, (2001).
Zhang, X. et al., "Cortisol and Cytokines in Chronic and Treatment-Resistant Patients with Schizophrenia: Association with Psychopathology and Response to Antipsychotics", Neuropsychopharmacology, 30(8):1532-1538, (2005).

* cited by examiner

METHODS FOR ADMINISTERING CORTICOSTEROIDS

Corticosteroids (CS) are a key part of therapy regimens for a diverse variety of conditions. Although corticosteroids are typically prescribed for a wide range of patients with inflammatory conditions, they are frequently prescribed for patients with respiratory conditions such as asthma or chronic obstructive pulmonary disease (COPD), vasculitides, skin diseases, musculoskeletal conditions, and neurological conditions. However, despite their clinical success, corticosteroids are used sparingly due to a broad array of serious adverse events including bone fractures, osteoporosis, hyperglycemia, and obesity amongst others.

11β-hydroxysteroid dehydrogenases (HSDs) are enzymes that regulate the intracellular levels of glucocorticoids. The HSD enzymes consist of two isoforms: the nicotinamide-adenine dinucleotide phosphate reduced-dependent type 1 (HSD1) in vivo generally converts inactive cortisone to active cortisol, and the nicotinamide-adenine dinucleotide dependent oxidative type 2 (HSD2) converts cortisol to cortisone.

It has been suggested that administration of a HSD1 selective inhibitor could potentially ameliorate side effects associated with corticosteroid administration, such as hyperglycemia, insulin resistance, obesity, hyperlipidemia, hypertension, and the like. However, there is a significant, unmet need for methods for administering corticosteroids, to a patient in need thereof which reduces the risk of side effects associated with such administration. The present disclosure fulfills these and other needs, as evident in reference to the following disclosure.

Polymyalgia rheumatica (PMR) and giant cell arteritis (GCA) are related inflammatory disorders of unknown etiology that may occur in persons aged 50 years and older. PMR typically presents acutely with bilateral upper extremity pain. GCA typically presents with unilateral or bilateral headache, myalgias, fatigue, fever, weight loss, and sometimes acute vision loss. PMR and GCA represent either different manifestations of the same disease or overlapping conditions. GCA may present as classic cranial (temporal) arteritis, large-vessel vasculitis, or single-organ arteritis. From 40% to 60% of patients diagnosed with GCA also have PMR, and 16% to 21% of PMR patients have GCA. PMR occurs 3 to 10 times more frequently than GCA. In 2008, an estimated 711 000 US residents had PMR and 228 000 had GCA. The highest incidence of PMR occurs in persons of northern European descent, ranging from 41 to 113 cases per 100 000 among persons aged 50 years and older. In the United States, GCA is the most frequent primary vasculitis with an incidence of 18 per 100 000. Women have a higher lifetime risk for PMR (2.4%) and GCA (1.0%) than men (1.7% for PMR and 0.5% for GCA) (Buttgereit et al., 2016). Oral corticosteroids (CS) have been the mainstay of PMR therapy for decades, and are the only medications indicated by FDA for PMR therapy. Clinical trials evidence for therapeutic efficacy in PMR (including for oral CS) is quite limited.

BRIEF SUMMARY

Figure 1:
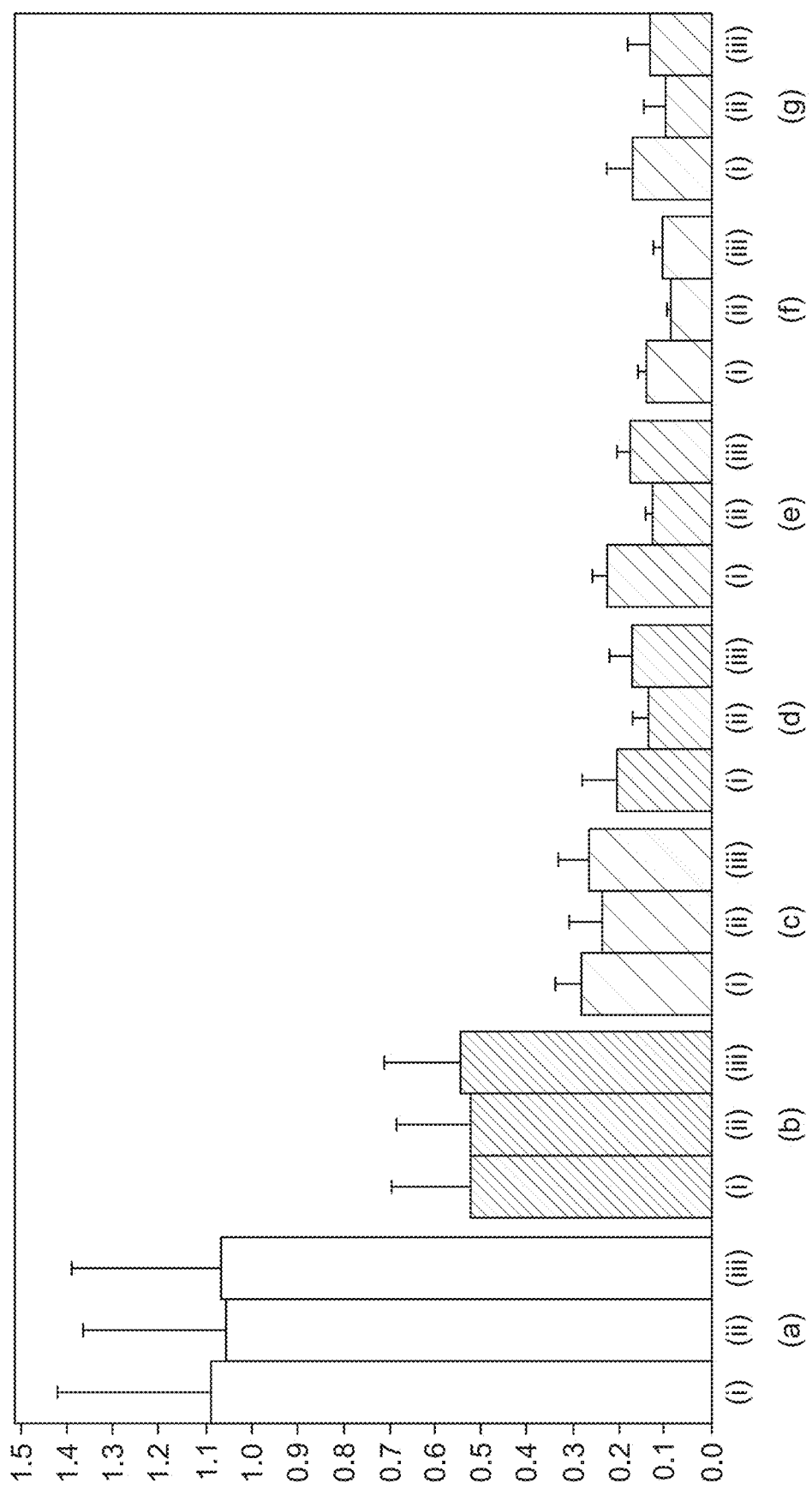
FIG. 1 shows the ratio of urinary (tetrahydrocortisol+allotetrahydrocortisol) to urinary tetrahydrocortisone for clinical trial subjects after a single dose of placebo or Compound A. (a) placebo; (b) 1 mg Compound A; (c) 3 mg Compound A; (d) 6 mg Compound A; (e) 10 mg Compound A; (f) 30 mg Compound A; (g) 60 mg Compound A. (i) 0-24 hr; (ii); 24-48 hr; (iii) 0-last. A lower value indicates inhibition of liver HSD1.

Provided is a method for administering a corticosteroid to a patient in need thereof, comprising:
  determining a target threshold for the ratio of urinary (tetrahydrocortisol+allotetrahydrocortisol) to urinary tetrahydrocortisone for the patient; and
  administering a HSD1 inhibitor to a patient who is being administered a corticosteroid,
  wherein:
    the corticosteroid is not prednisone; and
    the HSD1 inhibitor is administered at a first dose for a first time period, such that the administration is effective to maintain the patient's ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:

determining a target threshold for the ratio of urinary (tetrahydrocortisol+allotetrahydrocortisol) to urinary tetrahydrocortisone for the patient; and administering a HSD1 inhibitor to a patient who is being administered a corticosteroid, wherein:

the corticosteroid is not prednisone; and the HSD1 inhibitor is administered at a first dose for a first time period, such that the administration is effective to maintain the patient's ratio of urinary (tetrahydrocortisol+allotetrahydrocortisol) to urinary tetrahydrocortisone at a level below the target threshold.

Also provided is a method for administering a corticosteroid to a patient in need thereof, comprising:

determining a target threshold for the urinary ratio of urinary (tetrahydrocortisol+allotetrahydrocortisol) to urinary tetrahydrocortisone for the patient; and administering a HSD1 inhibitor to a patient who is being administered a corticosteroid, wherein:

the corticosteroid is not prednisone; and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:

determining a target threshold for the urinary ratio of urinary (tetrahydrocortisol+allotetrahydrocortisol) to urinary tetrahydrocortisone for the patient; and administering a HSD1 inhibitor to the patient who is being administered a corticosteroid, wherein:

the corticosteroid is not prednisone; and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

In some embodiments, an alternative method is used to determine HSD1 activity or occupancy.

These and other aspects of the invention will be apparent upon reference to the following detailed description. To this end, various references are set forth herein which describe in more detail certain background information, procedures, compounds, and compositions, and are each hereby incorporated by reference in their entirety.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Definitions

Also, as used in this specification and the appended claims, the singular forms "a," "an," and "the" include plural referents unless the content clearly dictates otherwise.

As used herein, "Compound A" refers to 4-{5-[1-(4-chloro-2,6-difluorophenoxy)-1-methylethyl]-4-methyl-4H-1,2,4-triazol-3-yl-3-fluorobenzamide, which has the structure:

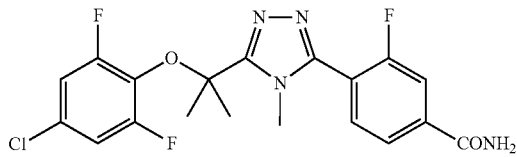 [SMILES: Cn1c(-c2ccc(C(N)=O)cc2F)nnc1C(C)(C)Oc1c(F)cc(Cl)cc1F]

As used herein, "Compound B" refers to N-[5-(aminocarbonyl) tricyclo[3.3.1.13,7]dec-2-yl]-α,α-dimethyl-4-[5-(trifluoromethyl)-2-pyridinyl]-1-piperazineacetamide.

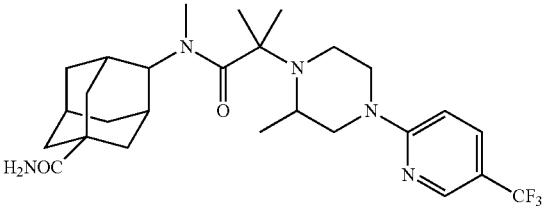 [SMILES: CC1CN(c2ccc(C(F)(F)F)cn2)CCN1C(C)(C)C(=O)N(C)C1C2CC3CC1CC(C(N)=O)(C3)C2]

As used herein, "co-administer" and "co-administration" and variants thereof mean the administration of at least two drugs to a patient either subsequently, simultaneously, or consequently proximate in time to one another (e.g., within the same day, or week or period of 30 days). When co-administered, two or more active agents can be co-formulated as part of the same composition or administered as separate formulations. This also may be referred to herein as "concomitant" administration or variants thereof.

As used herein, "administering to a patient" refers to the process of introducing a composition or dosage form into the patient via an art-recognized means of introduction.

As used herein the term "disorder" is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

As used herein, a "dose" means the measured quantity of an active agent to be taken at one time by a patient.

As used herein, "dosing regimen" means the dose of an active agent taken at a first time by a patient and the interval (time or symptomatic) at which any subsequent doses of the active agent are taken by the patient. The additional doses of the active agent can be different from the dose taken at the first time.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "patient" or "individual" or "subject" means a human, for whom or which therapy is desired, and generally refers to the recipient of the therapy.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "treating" or "treatment" refers to therapeutic applications to slow or stop progression of a disorder, prophylactic application to prevent development of a disorder, or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

Provided is a method for administering a corticosteroid to a patient in need thereof, comprising:
    determining a target threshold for the ratio of urinary (tetrahydrocortisol+allotetrahydrocortisol) to urinary tetrahydrocortisone for the patient; and
    administering a HSD1 inhibitor to a patient who is being administered a corticosteroid,
    wherein:
    the corticosteroid is not prednisone; and
    the HSD1 inhibitor is administered at a first dose for a first time period, such that the administration is effective to maintain the patient's ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:
    determining a target threshold for the ratio of urinary (tetrahydrocortisol+allotetrahydrocortisol) to urinary tetrahydrocortisone for the patient; and
    administering a HSD1 inhibitor to a patient who is being administered a corticosteroid,
    wherein:
    the corticosteroid is not prednisone; and
    the HSD1 inhibitor is administered at a first dose for a first time period, such that the administration is effective to maintain the patient's ratio of urinary (tetrahydrocortisol+allotetrahydrocortisol) to urinary tetrahydrocortisone at a level below the target threshold.

Also provided is a method for administering a corticosteroid to a patient in need thereof, comprising:
    determining a target threshold for the urinary ratio of urinary (tetrahydrocortisol+allotetrahydrocortisol) to urinary tetrahydrocortisone for the patient; and
    administering a HSD1 inhibitor to a patient who is being administered a corticosteroid, wherein:

the corticosteroid is not prednisone; and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:

determining a target threshold for the urinary ratio of urinary (tetrahydrocortisol+allotetrahydrocortisol) to urinary tetrahydrocortisone for the patient; and administering a HSD1 inhibitor to the patient who is being administered a corticosteroid, wherein:

the corticosteroid is not prednisone; and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

Also provided is a method for administering a corticosteroid to a patient in need thereof, comprising:

determining a target threshold for the ratio of urinary (tetrahydrocortisol+allotetrahydrocortisol) to urinary tetrahydrocortisone for the patient; and administering a HSD1 inhibitor to a patient who is being administered a corticosteroid, wherein:

the corticosteroid is not prednisone;

the HSD1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) or N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B); and the HSD1 inhibitor is administered at a first dose for a first time period, such that the administration is effective to maintain the patient's urinary ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:

determining a target threshold for the ratio of urinary (tetrahydrocortisol+allotetrahydrocortisol) to urinary tetrahydrocortisone for the patient; and administering a HSD1 inhibitor to a patient who is being administered a corticosteroid, wherein:

the corticosteroid is not prednisone;

the HSD1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) or N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B); and the HSD1 inhibitor is administered at a first dose for a first time period, such that the administration is effective to maintain the patient's urinary ratio of urinary (tetrahydrocortisol+allotetrahydrocortisol) to urinary tetrahydrocortisone at a level below the target threshold.

Also provided is a method for administering a corticosteroid to a patient in need thereof, comprising:

determining a target threshold for the urinary ratio of urinary (tetrahydrocortisol+allotetrahydrocortisol) to urinary tetrahydrocortisone for the patient; and administering a HSD1 inhibitor to a patient who is being administered a corticosteroid, wherein:

the corticosteroid is not prednisone;

the HSD1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) or N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B); and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

Also provided is a method for reducing or preventing the side effects associated with corticosteroid administration to a patient in need thereof, comprising:

determining a target threshold for the urinary ratio of urinary (tetrahydrocortisol+allotetrahydrocortisol) to urinary tetrahydrocortisone for the patient; and administering a HSD1 inhibitor to the patient who is being administered a corticosteroid, wherein:

the corticosteroid is not prednisone;

the HSD1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) or N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B); and the HSD1 inhibitor is administered at a first dose for a first time period, such that the administration is effective to reduce the patient's urinary ratio of urinary (tetrahydrocortisol+allotetrahydrocortisol) to urinary tetrahydrocortisone at a level below the target threshold.

In some embodiments, the HSD1 inhibitor is chosen from 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) and N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B), or a pharmaceutically acceptable salt thereof.

In some embodiments, the HSD1 inhibitor is Compound A, or a pharmaceutically acceptable salt thereof.

In some embodiments, the HSD1 inhibitor is Compound B, or a pharmaceutically acceptable salt thereof.

In some embodiments, the HSD1 inhibitor is AMG 221 ((5S)-2-[[(1R,3S,4S)-3-bicyclo[2.2.1]heptanyl]amino]-5-methyl-5-propan-2-yl-1,3-thiazol-4-one).

In some embodiments, the HSD1 inhibitor is Xanamem ((5-(1H-pyrazol-4-yl)thiophen-3-yl)((1R,3r,5S)-3-hydroxy-3-(pyrimidin-2-yl)-8-azabicyclo[3.2.1]octan-8-yl)methanone):

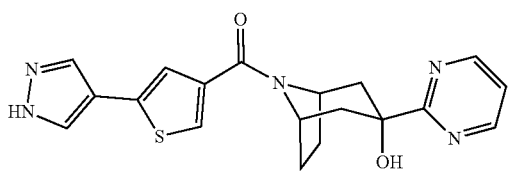 [SMILES: O=C(c1csc(-c2cn[nH]c2)c1)N1C2CCC1CC(O)(c1ncccn1)C2]

In some embodiments, the HSD1 inhibitor is a compound as disclosed in WO2013191396, WO2013058258, WO2012134233, or WO2011139107, each of which is hereby incorporated by reference in its entirety for all purposes.

In some embodiments, the target threshold for the ratio of urinary (tetrahydrocortisol+allotetrahydrocortisol) to urinary tetrahydrocortisone is chosen from about 0.2, about 0.3, about 0.4, about 0.5, and about 0.6. In some embodiments, the target threshold is about 0.2 and the patient has an additional risk factor. In some embodiments, the additional risk factor is chosen from diabetes, hypertension, elevated cholesterol, elevated triglycerides, nonalcoholic steatohepatitis, obesity, history of major adverse cardiovascular event, osteoporosis, osteonecrosis, ocular hypertension, or history of glaucoma. In some embodiments, the additional risk factor is age. In some embodiments, the additional risk factor is gender and the patient is female. In some embodiments, the additional risk factor is prior cumulative corticosteroid exposure. In some embodiments, the additional risk factor is a history of adverse events associated with corticosteroid administration.

In some embodiments, the target threshold for the ratio of urinary (tetrahydrocortisol+allotetrahydrocortisol) to urinary tetrahydrocortisone is about 0.66.

In some embodiments, the patient has been administered a corticosteroid for a period of time prior to being administered the HSD1 inhibitor.

In some embodiments, the patient is being administered the corticosteroid at a first dose for a first time period.

In some embodiments, the method further comprises administering a second dose of the corticosteroid to the patient.

In some embodiments, the second dose of the corticosteroid is a different amount than the first dose.

In some embodiments, the second dose of the corticosteroid is the same amount as the first dose.

In some embodiments, the corticosteroid is administered orally.

In some embodiments, the corticosteroid is administered intravenously or intramuscularly.

In some embodiments, the corticosteroid is administered intravenously. In some embodiments, the corticosteroid is administered intravenously and the HSD1 inhibitor is administered orally. In some embodiments, the corticosteroid is administered intravenously and the HSD1 inhibitor is administered orally at the same time as the intravenous administration of the corticosteroid. In some embodiments, the corticosteroid is administered intravenously and the HSD1 inhibitor is administered orally prior to the intravenous administration of the corticosteroid. In some embodiments, the corticosteroid is administered intravenously and the HSD1 inhibitor is administered orally in a manner sufficient to provide protection across multiple administrations of the corticosteroid, which may occur during a single day or more than one day. In some embodiments, the corticosteroid is administered intravenously and the HSD1 inhibitor is administered intravenously. In some embodiments, the corticosteroid and HSD1 inhibitor are co-formulated for intravenous administration. In some embodiments, the corticosteroid and HSD1 inhibitor are administered separately.

In some embodiments, the corticosteroid is administered intramuscularly. In some embodiments, the corticosteroid is administered intramuscularly at a frequency less than daily. In some embodiments, the corticosteroid is administered intramuscularly every other day. In some embodiments, the corticosteroid is administered intramuscularly twice a week. In some embodiments, the corticosteroid is administered intramuscularly once a week. In some embodiments, the corticosteroid is administered intramuscularly every other week. In some embodiments, the corticosteroid is administered intramuscularly and the HSD1 inhibitor is administered intramuscularly. In some embodiments, the corticosteroid and HSD1 inhibitor are co-formulated for intramuscular administration. In some embodiments, the corticosteroid and HSD1 inhibitor are administered separately. In some embodiments, the corticosteroid is administered intramuscularly and the HSD1 inhibitor is administered orally. In some embodiments, the corticosteroid is administered intramuscularly and the HSD1 inhibitor is administered orally as a single loading dose. In some embodiments, the corticosteroid is administered intramuscularly and the HSD1 inhibitor is administered orally as a single loading dose followed by one or more maintenance doses. In some embodiments, the corticosteroid is administered intramuscularly and the HSD1 inhibitor is administered orally as a plurality of doses, each of which may be the same amount or differing amounts.

In some embodiments, the corticosteroid is chosen from alclometasone, amcinonide, beclometasone, betamethasone, budesonide, ciclesonide, clobetasol, clocortolone, cloprednol, cortivazol, deflazacort, desonide, desoximetasone, dexamethasone, diflorasone, diflucortolone, difluprednate, fludrocortisone, fludroxycortide, flumetasone, flunisolide, fluocinolone, fluocinonide, fluocortin, fluocortolone, fluorometholone, fluperolone, fluticasone, fluprednidene, formocortal, halcinonide, halometasone, hydrocortisone, loteprednol, medrysone, methylprednisolone, mometasone, paramethasone, prednicarbate, prednisolone, prednylidene, rimexolone, tixocortol, triamcinolone, ulobetasol, combinations thereof, pharmaceutically acceptable salts thereof, and esters thereof.

In some embodiments, the corticosteroid is betamethasone or a pharmaceutically acceptable salt or ester thereof, and is administered at a dose of from about 0.25 to about 20 mg. In some embodiments, the corticosteroid is betamethasone or a pharmaceutically acceptable salt or ester thereof, and is administered at a dose of from about 0.6 to about 9 mg.

In some embodiments, the corticosteroid is prednisolone or a pharmaceutically acceptable salt or ester thereof, and is administered at a dose of from about 0.5 to about 200 mg. In some embodiments, the corticosteroid is prednisolone or a pharmaceutically acceptable salt or ester thereof, and is administered at a dose of from about 0.5 to 80 mg. In some embodiments, the corticosteroid is prednisolone or a pharmaceutically acceptable salt or ester thereof, and is administered at a dose of from about 0.5 to 60 mg. In some embodiments, the corticosteroid is prednisolone or a pharmaceutically acceptable salt or ester thereof, and the equivalent dosage of prednisolone is chosen from 1, 2.5, 5, 10, 20, and 30 mg.

In some embodiments, the corticosteroid is dexamethasone or a pharmaceutically acceptable salt or ester thereof, and is administered at a dose of from about 0.1 to about 40 mg. In some embodiments, the corticosteroid is dexamethasone or a pharmaceutically acceptable salt or ester thereof, and is administered at a dose of from about 0.1 to about 30 mg. In some embodiments, the corticosteroid is dexamethasone or a pharmaceutically acceptable salt or ester thereof, and is administered at a dose of from about 0.1 to about 20 mg. In some embodiments, the corticosteroid is dexamethasone or a pharmaceutically acceptable salt or ester thereof, and is administered at a dose of from about 0.1 to about 10 mg. In some embodiments, the corticosteroid is dexamethasone or a pharmaceutically acceptable salt or ester thereof, and is administered at a dose of from about 0.1 to about 9 mg.

In some embodiments, the corticosteroid is budesonide or a pharmaceutically acceptable salt or ester thereof, and is administered at a dose of from about 0.25 mg to 9 mg. In some embodiments, the corticosteroid is budesonide or a pharmaceutically acceptable salt or ester thereof, and is administered at a dosage chosen from the following:

In some embodiments, the corticosteroid is hydrocortisone or a pharmaceutically acceptable salt or ester thereof. In some embodiments, the corticosteroid is hydrocortisone or a pharmaceutically acceptable salt or ester thereof, and is administered at a dose of from about 20 to about 800 mg. In some embodiments, the corticosteroid is hydrocortisone or a pharmaceutically acceptable salt or ester thereof, and is administered at a dose of from about 20 to about 240 mg orally. In some embodiments, the corticosteroid is hydrocortisone or a pharmaceutically acceptable salt or ester thereof, and is administered at a dose of from about 20 to about 500 mg every two hours (e.g., for anti-inflammatory). In some embodiments, the corticosteroid is hydrocortisone or a pharmaceutically acceptable salt or ester thereof, and is administered at a dose of from about 20 to about 800 mg daily for the treatment of multiple sclerosis.

In some embodiments, the corticosteroid is deflazacort or a pharmaceutically acceptable salt or ester thereof, and is administered at a dose of from about 0.25 mg to about 1 mg/kg/day. In some embodiments, the corticosteroid is deflazacort or a pharmaceutically acceptable salt or ester thereof, and is administered at a dose of about 0.9 mg/kg/day.

In some embodiments, the corticosteroid is methylprednisolone or a pharmaceutically acceptable salt or ester thereof, and is administered orally at a dose of from about 0.4 to about 240 mg. In some embodiments, the corticosteroid is methylprednisolone or a pharmaceutically acceptable salt or ester thereof, and is administered intravenously at a dose of from about 10 to about 40 mg.

In some embodiments, the corticosteroid is methylprednisolone or a pharmaceutically acceptable salt or ester thereof, and is administered at a dose of 24 mg, followed by 20, 16, 12, 8, and 4 mg daily.

In some embodiments, the corticosteroid is administered at a dose equivalent to 1 mg prednisone. In some embodiments, the corticosteroid is administered at a dose equivalent to 2.5 mg prednisone. In some embodiments, the corticosteroid is administered at a dose equivalent to 5 mg prednisone. In some embodiments, the corticosteroid is administered at a dose equivalent to 10 mg prednisone. In some embodiments, the corticosteroid is administered at a dose equivalent to 20 mg prednisone. In some embodiments, the corticosteroid is administered at a dose equivalent to 30 mg prednisone.

In some embodiments, the side effects associated with corticosteroid administration are chosen from diabetes, fractures, obesity, Cushingoid appearance, hepatic steatosis, hypertension, hyperlipidemia, muscle weakness, dermal atrophy, impaired wound healing, osteoporosis/osteonecrosis, glaucoma, and mood/memory changes.

In some embodiments, the first dose of the HSD1 inhibitor is at least 0.7 mg. In some embodiments, the first dose of the HSD1 inhibitor is 0.7 mg. In some embodiments, the first dose of the HSD1 inhibitor is at least 1 mg. In some embodiments, the first dose of the HSD1 inhibitor is 1 mg. In some embodiments, the first dose of the HSD1 inhibitor is at least 2 mg. In some embodiments, the first dose of the HSD1 inhibitor is 2 mg. In some embodiments, the first dose of the HSD1 inhibitor is at least 2.5 mg. In some embodiments, the first dose of the HSD1 inhibitor is 2.5 mg. In some embodiments, the first dose of the HSD1 inhibitor is at least 3 mg. In some embodiments, the first dose of the HSD1 inhibitor is 3 mg. In some embodiments, the first dose of the HSD1 inhibitor is at least 4 mg. In some embodiments, the first dose of the HSD1 inhibitor is 4 mg. In some embodiments, the first dose of the HSD1 inhibitor is at least 5 mg. In some embodiments, the first dose of the HSD1 inhibitor is 5 mg. In some embodiments, the first dose of the HSD1 inhibitor is 6 mg.

In some embodiments, the first dose of the HSD1 inhibitor is sufficient to achieve the target threshold for the ratio of urinary (tetrahydrocortisol+allotetrahydrocortisol) to urinary tetrahydrocortisone. In some embodiments, the HSD1 inhibitor is administered at a single dose of 5 mg to achieve the target threshold. In some embodiments, the HSD1 inhibitor is administered at a dose of 6 mg to achieve the target threshold.

In some embodiments, multiple administrations are required to achieve the target threshold for the ratio of urinary (tetrahydrocortisol+allotetrahydrocortisol) to urinary tetrahydrocortisone. In some embodiments, the HSD1 inhibitor is administered at a dose of 2.5 mg for 2 days to achieve the target threshold. In some embodiments, the HSD1 inhibitor is administered at a dose of 2 mg for 3 days to achieve the target threshold. In some embodiments, the HSD1 inhibitor is administered at a dose of 1 mg for 5 days to achieve the target threshold. In some embodiments, the HSD1 inhibitor is administered at a dose of 0.7 mg for 7 days to achieve the target threshold.

In some embodiments, a second dose of the HSD1 inhibitor is not administered to the patient.

In some embodiments, the method further comprises administering a second dose of the HSD1 inhibitor. In some embodiments, prior to administering the second dose of the HSD1 inhibitor, the method further comprises measuring the ratio of urinary (tetrahydrocortisol+allotetrahydrocortisol) to urinary tetrahydrocortisone for the patient. In some embodiments, the method further comprising adjusting the dose of HSD1 inhibitor to maintain the patient's ratio of urinary (tetrahydrocortisol+allotetrahydrocortisol) to urinary tetrahydrocortisone at a level below the target threshold.

In some embodiments, the second dose of the HSD1 inhibitor is the same as the first dose of the HSD1 inhibitor.

In some embodiments, the second dose of the HSD1 inhibitor is more than the first dose of the HSD1 inhibitor.

In some embodiments, the second dose of the HSD1 inhibitor is less than the first dose of the HSD1 inhibitor.

In some embodiments, the target threshold for the ratio of urinary (tetrahydrocortisol+allotetrahydrocortisol) to urinary tetrahydrocortisone is about 0.2, and the first dose of the HSD1 inhibitor is the same amount as the second dose, i.e., the dosing amount is constant. In some embodiments, the first and second dose are 2 mg. In some embodiments, the first and second dose are 2.5 mg.

In some embodiments, the target threshold for the ratio of urinary (tetrahydrocortisol+allotetrahydrocortisol) to urinary tetrahydrocortisone is about 0.2, and the second dose of the HSD1 inhibitor is less than the first dose of the HSD1 inhibitor, e.g., the first dose is a loading dose and the second dose is a maintenance dose.

In some embodiments, e.g., when the target threshold for the ratio of urinary (tetrahydrocortisol+allotetrahydrocortisol) to urinary tetrahydrocortisone is 0.2, the first or loading dose is at least 3 mg, such as 3 mg. In some embodiments, the first or loading dose is at least 4 mg, such as 4 mg. In some embodiments, the first or loading dose is at least 5 mg, such as 5 mg. In some embodiments, the first or loading dose is at least 6 mg, such as 6 mg. In some embodiments, the second dose is 0.2 mg. In some embodiments, the second dose is 0.1 mg.

In some embodiments, e.g., when the target threshold for the ratio of urinary (tetrahydrocortisol+allotetrahydrocortisol) to urinary tetrahydrocortisone is 0.66, the first or loading dose is at least 0.7 mg, such as 0.7 mg. In some embodiments, e.g., when the target threshold is 0.66, the first or loading dose is at least 1 mg, such as 1 mg. In some embodiments, the first or loading dose is at least 2 mg, such as 2 mg. In some embodiments, the first or loading dose is at least 3 mg, such as 3 mg. In some embodiments, the first or loading dose is at least 4 mg, such as 4 mg. In some embodiments, the first or loading dose is at least 5 mg, such as 5 mg. In some embodiments, the first or loading dose is at least 6 mg. In some embodiments, the second dose is 0.2 mg. In some embodiments, the second dose is 0.1 mg.

In some embodiments, the corticosteroid is administered at decreasing levels over a period of time, e.g., a 6-day course of methylprednisolone in which patients take 6, 5, 4, 3, 2, and finally 1 dosage form on successive days, and the HSD1 inhibitor is administered at a dose of at least 0.833 mg with each corticosteroid dosage form. In some embodiments, the corticosteroid is methylprednisolone, the dosage form is a tablet, and each tablet is 4 mg. In some embodiments, the corticosteroid is formulated as a capsule.

In some embodiments, the HSD1 inhibitor is administered orally.

In some embodiments, the HSD1 inhibitor is provided in fixed dose combination ("FDC") tablets with the corticosteroid. In some embodiments, the FDC tablets are supplied for once daily dosage. In some embodiments, a course of once daily dosages is provided.

In some embodiments, the HSD1 inhibitor is provided for a dosing regimen consistent with sub-chronic treatment with a corticosteroid. In some embodiments, the subject will be instructed to take a decreasing count of tablets for a course of treatment. In some embodiments, the subject will be instructed to take a 6, 5, 4, 3, 2, and 1 tablets for the first, second, third, fourth, fifth, and sixth day of a six day once daily course of treatment.

In some embodiments, the HSD1 inhibitor is provided for a dosing regimen consistent with chronic treatment with a corticosteroid. In some embodiments, the subject will be instructed to take a single tablet for each day of a course of treatment. In some embodiments, the subject will be instructed to take two tablets for each day of a course of treatment. In some embodiments, the course of treatment is chosen from 2 weeks, 4 weeks, 1 month, 2 months, 3 months, 6 months, and 1 year.

In some embodiments, the HSD1 inhibitor is administered intravenously.

In some embodiments, the HSD1 inhibitor is administered daily, optionally with divided doses. In some embodiments, the HSD1 inhibitor is administered every other day.

In some embodiments, the corticosteroid is administered to treat a chronic disease or disorder. In some embodiments, the corticosteroid is administered to treat an acute disease or disorder.

In some embodiments, the corticosteroid is administered to treat a disease or disorder chosen from:
  endocrine disorders, such as primary or secondary adrenocortical insufficiency, congenital adrenal hyperplasia, nonsuppurative thyroiditis, and hypercalcemia associated with cancer;
  rheumatic disorders, such as adjunctive therapy for short-term administration (to tide the patient over an acute episode or exacerbation) in psoriatic arthritis, rheumatoid arthritis, ankylosing spondylitis, acute and subacute bursitis, acute nonspecific tenosynovitis, acute gouty arthritis, post-traumatic osteoarthritis, synovitis of osteoarthritis, acute rheumatic carditis, dermatomyositis, temporal arteritis, polymyositis, and systemic lupus erythematosus and epicondylitis;
  collagen diseases, such as during an exacerbation or as maintenance therapy in selected cases of systemic lupus erythematosus, systemic dermatomyositis (polymyositis), and acute rheumatic carditis;
  dermatologic diseases, such as pemphigus, bullous dermatitis herpetiformis, severe erythema multiforme Stevens-Johnson syndrome), exfoliative dermatitis, exfoliative erythroderma, mycosis fungoides, severe psoriasis, and severe seborrheic dermatitis;
  allergic states, such as control of severe or incapacitating allergic conditions intractable to adequate trials of conventional treatment such as seasonal or perennial allergic rhinitis, bronchial asthma, contact dermatitis, atopic dermatitis, serum sickness, transfusion reactions, and drug hypersensitivity reactions;
  ophthalmic diseases, such as severe acute and chronic allergic and inflammatory processes involving the eye and its adnexa such as allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis, ocular inflammatory conditions unresponsive to topical corticosteroids, and iridocyclitis;
  respiratory diseases, such as symptomatic sarcoidosis, Loeffler's syndrome not manageable by other means, berylliosis, fulminating or disseminated pulmonary tuberculosis when used concurrently with appropriate antituberculous chemotherapy, idiopathic eosinophilic pneumonias, symptomatic sarcoidosis, and aspiration pneumonitis;
  hematologic disorders, such as idiopathic thrombocytopenic purpura in adults, secondary thrombocytopenia in adults, acquired (autoimmune) hemolytic anemia, erythroblastopenia (RBC anemia), pure red cell aplasia, and congenital (erythroid) hypoplastic anemia;
  neoplastic diseases, such as for palliative management of leukemias and lymphomas in adults and acute leukemia of childhood;
  edematous states, such as to induce a diuresis or remission of proteinuria in the nephrotic syndrome, without uremia, of the idiopathic type or that due to lupus erythematosus;

gastrointestinal diseases, such as to tide the patient over a critical period of the disease in: ulcerative colitis or regional enteritis;

nervous system, such as acute exacerbations of multiple sclerosis, cerebral edema associated with primary or metastatic brain tumor, or craniotomy;

renal diseases, such as to induce diuresis or remission of proteinuria in idiopathic nephrotic syndrome or that due to lupus erythematosus; and other diseases or disorders such as tuberculous meningitis with subarachnoid block or, impending block when used concurrently with appropriate antituberculous chemotherapy, and trichinosis with neurologic or myocardial involvement.

In some embodiments, the corticosteroid is administered to treat vasculitis, e.g., Behcet's disease, central nervous system vasculitis, cryogloblinemia, Churg-Strauss syndrome, giant cell arteritis (GCA), granulomatosis with polyangiitis, Henoch-Schönlein purpura, hypersensitivity vasculitis, aortitis, microscopic polyangiitis, polyarteritis nodosa, polymyalgia rheumatica (PMR), rheumatoid vasculitis, Takayasu's arteritis, and urticarial vasculitis.

In certain embodiments, the vasculitis is chosen from GCA and PMR.

In certain embodiments, the GCA is new-onset GCA.
In certain embodiments, the GCA is ongoing GCA.
In certain embodiments, the PMR is new-onset PMR.
In certain embodiments, the PRM is ongoing PMR.

In certain embodiments, coadministration of the HSD1 inhibitor and the corticosteroid is effective at alleviating adverse effects that arise from administration of corticosteroid. In certain embodiments, the adverse effects are chosen from one or more of the following: diabetes, impaired glucose tolerance, insulin resistance, weight gain, lipodystrophy, hepatic steatosis, elevated blood pressure, increased blood lipids, muscle atrophy, skin atrophy, impaired wound healing, bone fracture, osteoporosis, glaucoma, elevated intraocular pressure, memory deficits, mood changes, and hypothalamic-pituitary-adrenal (HPA) axis suppression.

Alternative Methods

The foregoing has focused on methods for measuring HSD1 activity using the urinary metabolite ratio, i.e., the ratio of urinary (tetrahydrocortisol+allotetrahydrocortisol) to urinary tetrahydrocortisone for the patient. In some embodiments, an alternative method is used to measure HSD1 activity.

In some embodiments, HSD1 activity is measured using a ratio of mass-labeled cortisol and cortisone in the blood, e.g., the plasma, or in the cerebrospinal fluid. In some embodiments, the method as disclosed by Basu for measuring CS levels in the hepatic and portal veins is utilized. See Basu, et al. (2009) Diabetes 58: 39-45, which is incorporated herein by reference for all purposes. In some embodiments, HSD1 activity is measured by a jugular mass-labeled cortisol:cortisone ratio. In some embodiments, [9,11,12,12-$^2$H$_4$] cortisol (D4 cortisol) is used to characterize HSD1 inhibition as a precursor of the HSD1 substrate [9,12,12-$^2$H$_3$] cortisone (D3 cortisone) and the HSD1 product [9,12,12-$^2$H$_3$] cortisol (D3 cortisol). See, Katz, et al. (2013) Transl. Psychiatry 3(8):e295, which is incorporated herein by reference for all purposes.

In some embodiments, HSD1 activity is measured using a ratio of active and inactive forms of a corticosteroid medication in the blood, e.g., the plasma, or in the cerebrospinal fluid. In some embodiments, prednisone is used to characterize HSD1 inhibition as a precursor of the HSD1 product prednisolone.

In some embodiments, HSD1 activity is measured by conversion of a HSD1 substrate to a HSD1 product in a fat biopsy. In some embodiments, the HSD1 substrate is mass labeled cortisone and the HSD1 product is mass labeled cortisol. In some embodiments, the HSD1 substrate is [9,12,12-$^2$H$_3$] cortisone (D3 cortisone) and the HSD1 product is [9,12,12-$^2$H$_3$] cortisol (D3 cortisol). In some embodiments, the HSD1 substrate is an 11-keto corticosteroid and that HSD1 product is an 11-hydroxy corticosteroid. In some embodiments, the HSD1 substrate is prednisone and the HSD1 product is prednisolone.

In some embodiments, HSD1 occupancy is measured rather than HSD1 activity or inhibition. Accordingly, also provided is a method for administering a corticosteroid to a patient in need thereof, comprising:

determining a target HSD1 occupancy by HSD1 inhibitor for the patient; and administering a HSD1 inhibitor to a patient who is being administered a corticosteroid, wherein:

the corticosteroid is not prednisone; and the HSD1 inhibitor is administered at a first dose for a first time period, such that the administration is effective to maintain the patient's target HSD1 occupancy by HSD1 inhibitor at a level below the target threshold.

Also provided is a method for reducing or preventing the side effects associated with corticosteroid administration to a patient in need thereof, comprising:

determining a target HSD1 occupancy by HSD1 inhibitor for the patient; and administering a HSD1 inhibitor to a patient who is being administered a corticosteroid, wherein:

the corticosteroid is not prednisone; and the HSD1 inhibitor is administered at a first dose for a first time period, such that the administration is effective to maintain the patient's target HSD1 occupancy by HSD1 inhibitor at a level below the target threshold.

Also provided is a method for administering a corticosteroid to a patient in need thereof, comprising:

determining a target HSD1 occupancy by HSD1 inhibitor for the patient; and administering a HSD1 inhibitor to the patient who is being administered a corticosteroid, wherein:

the corticosteroid is not prednisone; and the HSD1 inhibitor is administered at a first dose for a first time period, such that the administration is effective to reduce the patient's target HSD1 occupancy by HSD1 inhibitor at a level below the target threshold.

Also provided is a method for reducing or preventing the side effects associated with corticosteroid administration to a patient in need thereof, comprising:

determining a target HSD1 occupancy by HSD1 inhibitor for the patient; and administering a HSD1 inhibitor to a patient who is being administered a corticosteroid, wherein:

the corticosteroid is not prednisone; and the HSD1 inhibitor is administered at a first dose for a first time period, such that the administration is effective to reduce the patient's target HSD1 occupancy by HSD1 inhibitor at a level below the target threshold.

In some embodiments, the patient's target HSD1 occupancy by HSD1 inhibitor is reduced to a level below the target threshold within 21 days. In some embodiments, the patient's target HSD1 occupancy by HSD1 inhibitor is reduced to a level below the target threshold within 14 days. In some embodiments, the patient's target HSD1 occupancy by HSD1 inhibitor is reduced to a level below the target threshold within 2-11 days. In some embodiments, the patient's target HSD1 occupancy by HSD1 inhibitor is reduced to a level below the target threshold within 5-7 days. In some embodiments, the patient's target HSD1 occupancy by HSD1 inhibitor is reduced to a level below the target threshold within 7 days. In some embodiments, the patient's target HSD1 occupancy by HSD1 inhibitor is reduced to a level below the target threshold within 3-4 days. In some embodiments, the patient's target HSD1 occupancy by HSD1 inhibitor is reduced to a level below the target threshold within 4 days. In some embodiments, the patient's target HSD1 occupancy by HSD1 inhibitor is reduced to a level below the target threshold within 3 days. In some embodiments, the patient's target HSD1 occupancy by HSD1 inhibitor is reduced to a level below the target threshold within 2 days. In some embodiments, the patient's target HSD1 occupancy by HSD1 inhibitor is reduced to a level below the target threshold within a single day.

In some embodiments, the target HSD1 occupancy is 80%. In some embodiments, the target HSD1 occupancy is 90%. In some embodiments, the HSD1 occupancy is determined for the brain. In some embodiments, the HSD1 occupancy is determined for adipose tissue. In some embodiments, the HSD1 occupancy is determined for liver. In some embodiments, the HSD1 occupancy is determined for more than one tissue. In some embodiments, the HSD1 occupancy is determined from using an imaging method. In some embodiments, the imaging method is positron emission tomography ("PET") following administration of a radiolabeled HSD1 ligand as a tracer. In some embodiments, the HSD1 ligand is [$^{11}$C] AS2471907 (3-(2-chlorophenyl)-4-(methyl-$^{11}$C)-5-[2-[2,4,6-trifluorophenoxy]propan-2-yl]-4H-1,2,4-triazole). In some embodiments, the imaging method is similar to the method disclosed in Gallezot, J.-D. J Nucl. Med. 2019, jnumed-118. In some embodiments, the HSD1 occupancy in adipose tissue is determined from a biopsy of adipose tissue.

Pharmaceutical Products

Also provided is a pharmaceutical product comprising a HSD1 inhibitor and a corticosteroid, wherein the corticosteroid is not prednisone; and the HSD1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A) or N-[5-(aminocarbonyl) tricyclo[3.3.1.13,7]dec-2-yl]-α,α-dimethyl-4-[5-(trifluoromethyl)-2-pyridinyl]-1-piperazineacetamide (Compound B).

In some embodiments, the pharmaceutical product is for intravenous or intramuscular administration.

In some embodiments, the pharmaceutical product is for oral administration.

In some embodiments, the pharmaceutical product comprises a combined preparation wherein the HSD1 inhibitor and the corticosteroid are co-formulated.

In some embodiments, the combined preparation is a tablet having two or more layers, wherein each of the HSD1 inhibitor and the corticosteroid are in different layers, optionally separated by a barrier layer.

In some embodiments, the combined preparation is a tablet having a core-shell configuration wherein the core comprises the HSD1 inhibitor and the shell comprises the corticosteroid, wherein the core and shell are optionally separated by a barrier layer.

In some embodiments, the combined preparation is a tablet having a core-shell configuration wherein the core comprises the corticosteroid and the shell comprises the HSD1 inhibitor, wherein the core and shell are optionally separated by a barrier layer.

In some embodiments, the combined preparation is a capsule containing the HSD1 inhibitor and the corticosteroid.

In some embodiments, the combined preparation is a combination of mini-tablets comprising the HSD1 inhibitor and mini-tablets comprising the corticosteroid.

In some embodiments, the pharmaceutical product comprises a combined preparation wherein the HSD1 inhibitor and the corticosteroid are co-packaged.

In some embodiments, the HSD1 inhibitor is formulated for oral administration and the corticosteroid is administered for intramuscular administration.

In some embodiments, the HSD1 inhibitor is Compound A, and is formulated for oral administration. In some embodiments, the HSD1 inhibitor is Compound B, and is formulated for oral administration.

In some embodiments, the HSD1 inhibitor is formulated as oral tablets. In some embodiments, the HSD1 inhibitor is formulated as oral tablets with a dosage of the HSD1 inhibitor chosen from 0.1, 0.2, 0.4, 0.7, 1.0, 1.5, 2.0, 2.5, 3.0, 3.5, 4.0, 4.5, 5.0, 5.5 and 6.0 mg. In some embodiments, the HSD1 inhibitor is formulated as oral tablets with Compound A. In some embodiments, the HSD1 inhibitor is formulated as oral tablets with Compound B.

In some embodiments, the pharmaceutical product comprises a twin pack.

In some embodiments, the pharmaceutical product comprises a kit comprising a first portion comprising the HSD1 inhibitor and a second portion comprising the corticosteroid. In some embodiments, the pharmaceutical product comprises a kit comprising a dosage form of HSD1 inhibitor at a loading dose and one or more dosage forms of the HSD1 inhibitor at a maintenance dose and one or more dosage forms of the corticosteroid.

In some embodiments, the pharmaceutical product comprises the following: (1) a loading dose of the HSD1 inhibitor together with six dosage forms comprising an amount of corticosteroid, which is to be administered on the first day; (2) a maintenance dose of the HSD1 inhibitor together with five dosage forms comprising the corticosteroid, which is to be administered on the second day; (3) a maintenance dose of the HSD1 inhibitor together with four dosage forms comprising the corticosteroid, which is to be administered on the third day; (4) a maintenance dose of the HSD1 inhibitor together with three dosage forms comprising the corticosteroid, which is to be administered on the fourth day; (5) a maintenance dose of the HSD1 inhibitor together with two dosage forms comprising the corticosteroid, which is to be administered on the fifth day; and (6) a maintenance dose of the HSD1 inhibitor together with one dosage form comprising the corticosteroid, which is to be administered on the sixth day.

In some embodiments, the loading dose of the HSD1 inhibitor is administered as six split doses wherein one of the split doses is administered with each of the dosage forms comprising the corticosteroid. In some embodiments, the split dose is co-formulated with the dosage form comprising the corticosteroid. In some embodiments, the maintenance dose of the HSD1 inhibitor is administered as split doses with each of the split doses co-formulated with the dosage forms comprising the corticosteroid. For example, on the third day, the maintenance dose of the HSD1 inhibitor is divided into four split doses, with each of the split doses being administered with a dosage form of the corticosteroid. In some embodiments, the split maintenance dose of the HSD1 inhibitor is co-formulated with the corticosteroid.

In some embodiments, the pharmaceutical product further comprises one or more excipients. Conventional excipients, such as binding agents, fillers, acceptable wetting agents, tabletting lubricants, and disintegrants can be used in tablets and capsules for oral administration.

Compositions for oral administration can be in the form of solutions, emulsions, aqueous or oily suspensions, and syrups. Alternatively, the compositions for oral administration can be in the form of dry powder that can be reconstituted with water or another suitable liquid vehicle before use. Additional additives such as suspending or emulsifying agents, non-aqueous vehicles (including edible oils), preservatives, and flavorings and colorants can be added. Compositions for intravenous or intramuscular administration can be prepared by dissolving the compounds in a suitable liquid vehicle and filter sterilizing the solution before filling and sealing an appropriate vial or ampoule. These are just a few examples of the many appropriate methods well known in the art for preparing compositions for oral, intravenous or intramuscular administration.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Example 1: Liver Inhibition by Compound A

Following a minimum of a 10-hour fast, healthy adult racially diverse male and female subjects were administered Compound A (ASP3662) or placebo for Compound A with 240 mL of room temperature water. Subjects continued to fast from any food and drinks (water was allowed as desired except for 1 hour before and 1 hour after study drug administration) until 4 hours after study drug administration. Urine samples were collected for the measurement of cortisol, cortisone, tetrahydrocortisol (5α, 5β) and tetrahydrocortisone. The cumulative amount of each entity excreted in the urine was calculated for each subject from time zero to 24 hours after dosing (Ae24), from 24 hours after dosing to 48 hours after dosing (Ae48), and Aelast. Data are presented in FIG. 1.

The ratio of 5α-tetrahydrocortisol+5β-tetrahydrocortisol to urinary tetrahydrocortisone was used as an indicator of HSD-1 activity. Compound A decreased the 5α-tetrahydrocortisol+5β-tetrahydrocortisol to urinary tetrahydrocortisone ratio with increasing dose compared to placebo, resulting in approximately 80% inhibition at 6 mg. Increasing the dose above 6 mg did not substantially increase the level of inhibition.

Healthy adult Japanese male and female subjects were administered Compound A or placebo for compound A after a standard breakfast daily. A single dose was administered on Day 1, followed by daily doses on Days 5 through 18. Urine samples were collected for 24 hours on Day 1 and Day 18. Doses of 10 mg, 20 mg and 50 mg Compound A significantly decreased HSD-1 activity on both days 1 and 18 with a mean ratio of approximately 0.1 to 0.2.

| | Compound A | | | |
|---|---|---|---|---|
| | Placebo | 10 mg | 20 mg | 50 mg |
| N | 6 | 8 | 8 | 8 |
| HSD-1 ratio (tetrahydrocortisol [5α + 5β]/ tetrahydrocortisone) | | | | |
| Day 1 mean | 1.04 | 0.18 | 0.14 | 0.14 |
| Day 1 SD | 0.286 | 0.056 | 0.029 | 0.034 |
| Day 1 Median | 0.96 | 0.19 | 0.14 | 0.14 |
| Day 1 Range | 0.76-1.56 | 0.09-0.24 | 0.07-0.15 | 0.11-0.21 |
| Day 18 Mean | 1.09 | 0.13 | 0.09 | 0.10 |
| Day 18 SD | 0.423 | 0.038 | 0.025 | 0.024 |
| Day 18 Median | 0.97 | 0.12 | 0.10 | 0.09 |
| Day 18 Range | 0.64-1.78 | 0.07-0.18 | 0.05-0.13 | 0.07-0.14 |

Healthy adult non-Japanese male and female subjects were administered Compound A or placebo for compound A after a standard breakfast. A single dose was administered on Day 1, followed by daily doses on Days 5 through 18. Urine samples were collected for 24 hours on Day 1 and Day 18. Doses of 20 mg and 50 mg Compound A significantly decreased HSD-1 activity on both days 1 and 18 with a mean ratio of approximately 0.1.

| | Compound A | | |
|---|---|---|---|
| | Placebo | 20 mg | 50 mg |
| N | 4 (3 on Day 18) | 8 | 8 (7 on Day 18) |
| HSD-1 ratio (tetrahydrocortisol [5α + 5β]/ tetrahydrocortisone) | | | |
| Day 1 mean | 1.01 | 0.17 | 0.16 |
| Day 1 SD | 0.200 | 0.085 | 0.040 |
| Day 1 Median | 0.94 | 0.16 | 0.16 |
| Day 1 Range | 0.87-1.29 | 0.09-0.37 | 0.11-0.22 |
| Day 18 Mean | 1.07 | 0.12 | 0.11 |
| Day 18 SD | 0.226 | 0.030 | 0.023 |
| Day 18 Median | 0.94 | 0.12 | 0.10 |
| Day 18 Range | 0.94-1.33 | 0.08-0.15 | 0.09-0.16 |

Elderly non-Japanese male and female subjects in general good health were administered Compound A or placebo for compound A after a standard breakfast. A single dose was administered on Day 1, followed by daily doses on Days 5 through 18. Urine samples were collected for 24 hours on Day 1 and Day 18. Doses of 20 mg Compound A significantly decreased HSD-1 activity on both days 1 and 18 with a mean ratio of approximately 0.1.

| | Compound A | |
|---|---|---|
| | Placebo | 20 mg |
| N | 3 | 9 |
| Day 1 Mean | 0.91 | 0.17 |
| Day 1 SD | 0.199 | 0.034 |
| Day 1 Median | 0.89 | 0.16 |
| Day 1 Range | 0.72-1.12 | 0.14-0.21 |
| Day 18 Mean | 0.82 | 0.11 |
| Day 18 SD | 0.052 | 0.026 |
| Day 18 Median | 0.83 | 0.11 |
| Day 18 Range | 0.77-0.87 | 0.08-0.16 |

Figure 2:
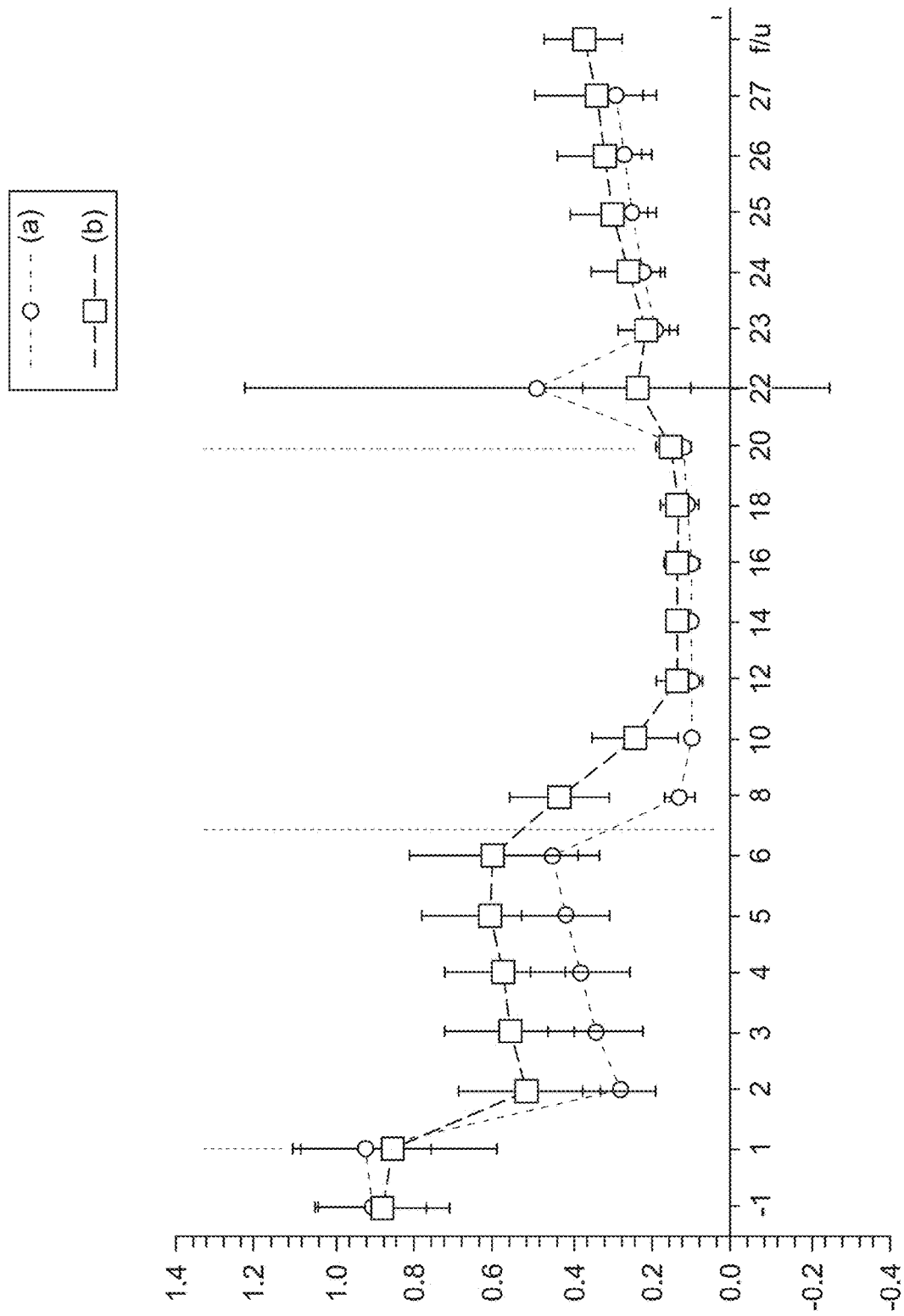
FIG. 2 shows the ratio of urinary (tetrahydrocortisol+allotetrahydrocortisol) to urinary tetrahydrocortisone for clinical trial subjects prior to, and after single (on Day 1) and multiple (daily on Days 5 through 18) doses of Compound A. (a) 2.0 mg and (b) 0.7 mg of Compound A. A lower value indicates inhibition of liver HSD1. The abscissa is labeled as Day, where −1 is prior to the first dose of study drug.
Figure 3:
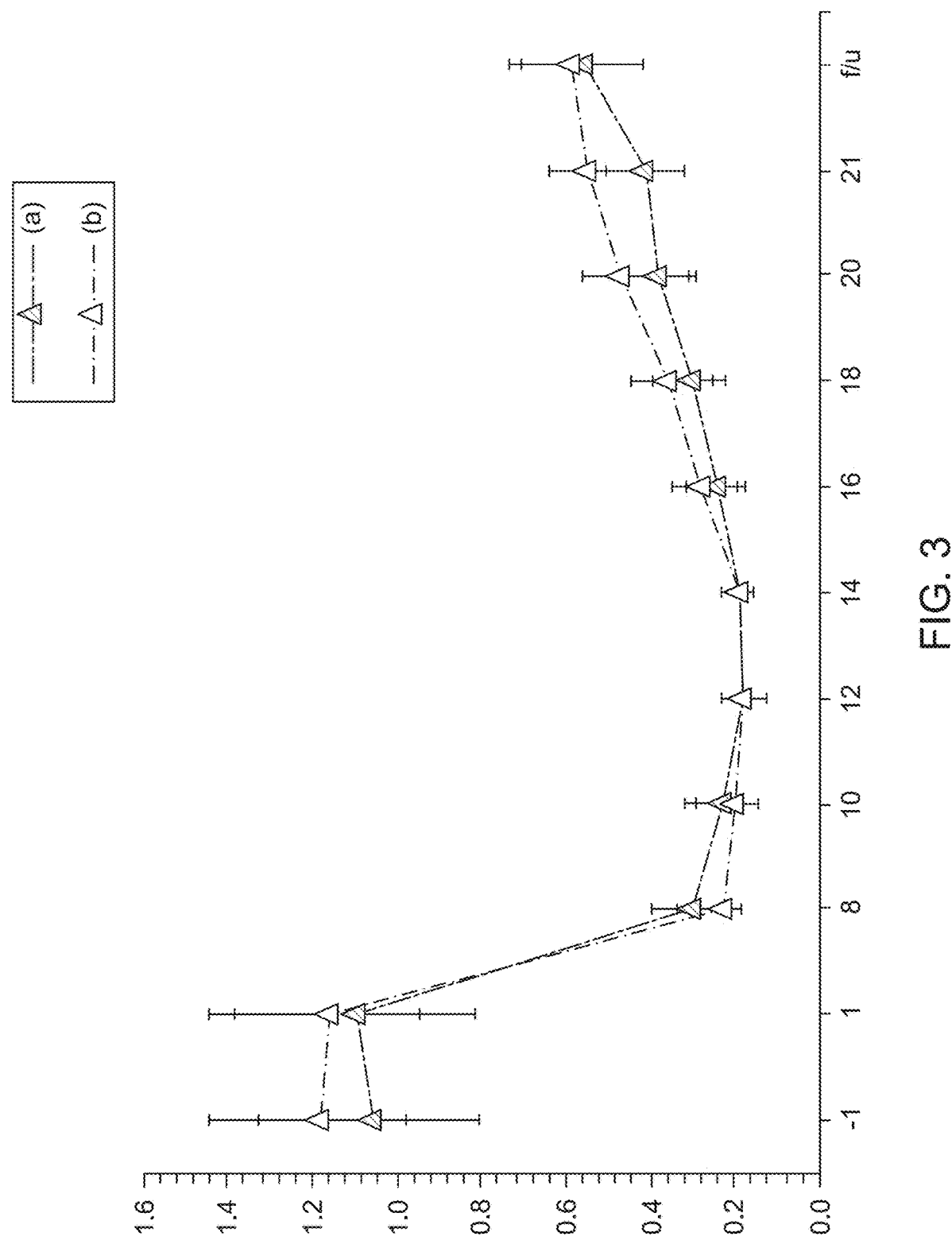
FIG. 3 shows the ratio of urinary (tetrahydrocortisol+allotetrahydrocortisol) to urinary tetrahydrocortisone for clinical trial subjects prior to, and after single (on Day 1) and multiple (daily on Days 2 through 14) doses of Compound A. (a) 0.4 mg and (b) 0.2 mg of Compound A. A lower value indicates inhibition of liver HSD1. The abscissa is labeled as Day, where −1 is prior to the first dose of study drug.

Healthy adult non-Japanese male and female subjects were administered Compound A after a standard breakfast. A single dose was administered on Day 1, followed by daily doses on Days 7 through 20 (2 mg and 0.7 mg cohorts, FIG. 2) or on Days 2 through 14 (0.4 and 0.2 mg cohorts, FIG. 3).

Urine samples were collected on multiple days. Compound A significantly decreased HSD-1 activity.

Example 2: Population Pharmacokinetics Model for Compound A

Figure 4:
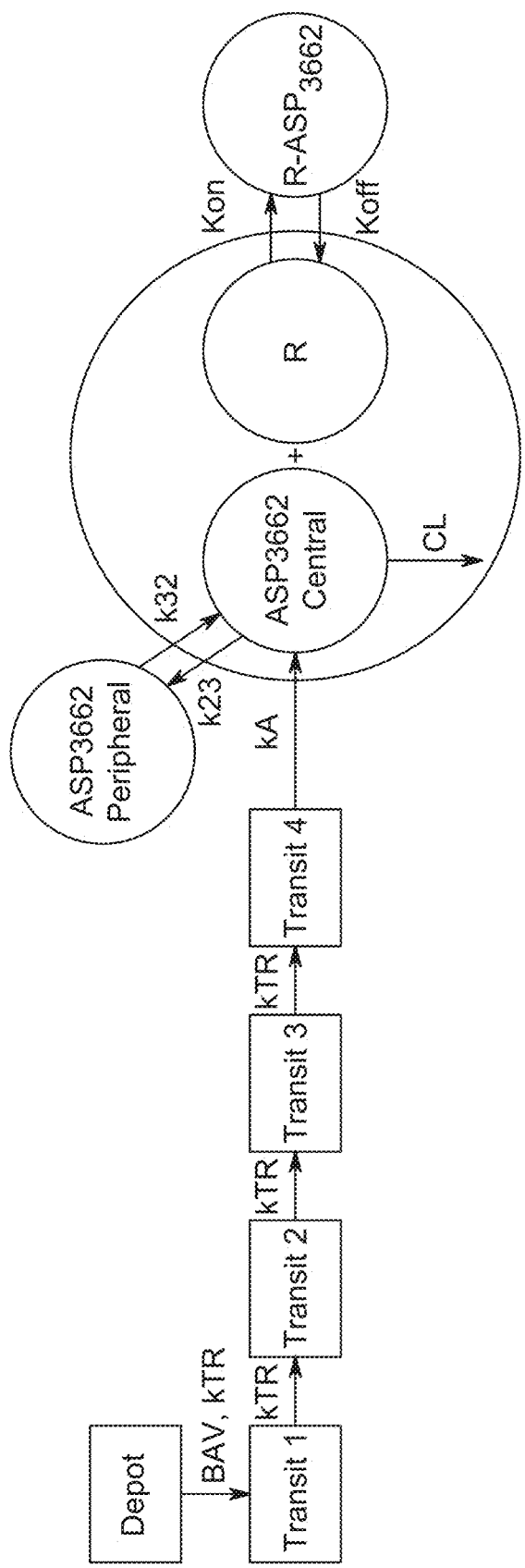
FIG. 4 provides a schematic of the population pharmacokinetics model for Compound A, with 4-compartment transient absorption, saturable binding from the central compartment, and first-order elimination.

On the basis of data from two Compound A clinical trials, a population pharmacokinetics model (FIG. 4) was developed using a maximal dose of 20 mg. The selected model to describe the pharmacokinetics of Compound A was a two-compartment disposition model, with a 4-compartment transit absorption, saturable binding from the central compartment, and first-order elimination. Inter-individual variability was implemented on clearance (CL), volume of distribution (V2), absorption rate constant (kA), second order association constant (Kon), first order dissociation constant (Koff), and total number of saturable binding receptors (R). This model had satisfactory goodness-of-fit and acceptable relative standard errors.

CL, kA, R, Kon, and Koff are defined above. BAV is relative bioavailability, kTR is a transit rate constant (equal to kA), k23 and k32 are transfer rate constants between central and peripheral compartments.

In exploratory covariate analysis, age was found to have a statistically significant impact on BAV. The covariate effect was moderate (25% increase of BAV in 88-year old subjects compared to 36-year old subjects). Bodyweight also had an impact on Compound A parameters through allometric scaling.

| Parameter | Estimate | Relative standard error (%) | Inter-individual variability (%) | Standard error of IIV (%) |
|---|---|---|---|---|
| CL (L/h/(70 kg)$^{0.75}$) | 7.24 | 4.7 | 38.6 | 19.7 |
| V2 (L/70 kg) | 90.2 | 3.5 | 23.2 | 21.6 |
| k23 (h$^{-1}$/(70 kg)$^{-0.25}$) | 0.00341 | 6.3 | | |
| k32 (h$^{-1}$/(70 kg)$^{-0.25}$) | 0.0255 | 4.0 | | |
| kA (h$^{-1}$) | 5.38 | 5.4 | 47.2 | 17.6 |
| Kon (µg$^{-1}$ · h$^{-1}$) | 0.0682 | 6.9 | 111 | 20.0 |
| Koff (h$^{-1}$) | 0.210 | 9.8 | 138 | 34.6 |
| R (nmol) | 3170 | 4.2 | 30.8 | 23.0 |
| Covariate: age on BAV | 0.200 | 29.9 | | |
| Log additive residual error | 0.254 | 0.015 | | |

The estimated total number of saturable binding receptors corresponds to 1.347 mg of Compound A.

Example 3: Brain Occupancy by Compound A

The level and time course of HSD-1 occupancy following single dose administration of Compound A were assessed in healthy male subjects by positron emission tomography (PET). For each PET scan, [11C]AS2471907 was administered by an intravenous infusion pump, followed by up to 120 minutes of dynamic PET data acquisition. Most subjects underwent two PET scans. Enzyme occupancy was determined using occupancy plots that did not assume a reference region with specific binding.

Single doses of 30 and 6 mg Compound A were associated with >96% region of interest size weighted average (ROIswa) HSD-1 occupancy at scan times that ranged from 2.62 to 46.75 hours post Compound A dose. A single dose of 3 mg Compound A was associated with HSD-1 occupancy of ~90% at 3.25 hours, ~86% at 19.2-25.43 hours, ~60-80% at 42.19-46.24 hours, ~40% at 138.67-139.36 hours, and 26% at 189.15 hours post Compound A dose. In contrast, no enzyme occupancy was detected following single 2 and 1 mg Compound A doses.

| | | PET Scan 1 | | PET Scan 2 | |
|---|---|---|---|---|---|
| Subject | Compound A Dose (mg) | Time (hrs post dose) | Occupancy (ROIswa) | Time (hrs post dose) | Occupancy (ROIswa) |
| A | 30 | 2.62 | 99.68 | 23.75 | 99.71 |
| B | 30 | 27.43 | 99.97 | 46.75 | 98.83 |
| C | 6 | 3.25 | 99.73 | 23.74 | 96.20 |
| D | 3 | 3.27 | 89.91 | 45.25 | 83.15 |
| E | 3 | 19.2 | 88.16 | 25.43 | 83.85 |
| F | 3 | 42.19 | 58.87 | 138.67 | 45.49 |
| G | 3 | 42.46 | 70.96 | 189.15 | 25.61 |
| H | 3 | 43.85 | 56.39 | 139.36 | 36.31 |
| I | 3 | 46.24 | 60.92 | Not done | |
| J | 2 | 2.84 | <0 | Not done | |
| K | 1 | 3.24 | <0 | 20.66 | <0 |
| L | 1 | 22.55 | <0 | 47.95 | <0 |

Example 4: Simulated HSD-1 Inhibition by Compound A

Simulations of brain enzyme occupancy were conducted for several dosing schemes for Compound A that involved both an initial dose and a maintenance dose.

Figure 5:
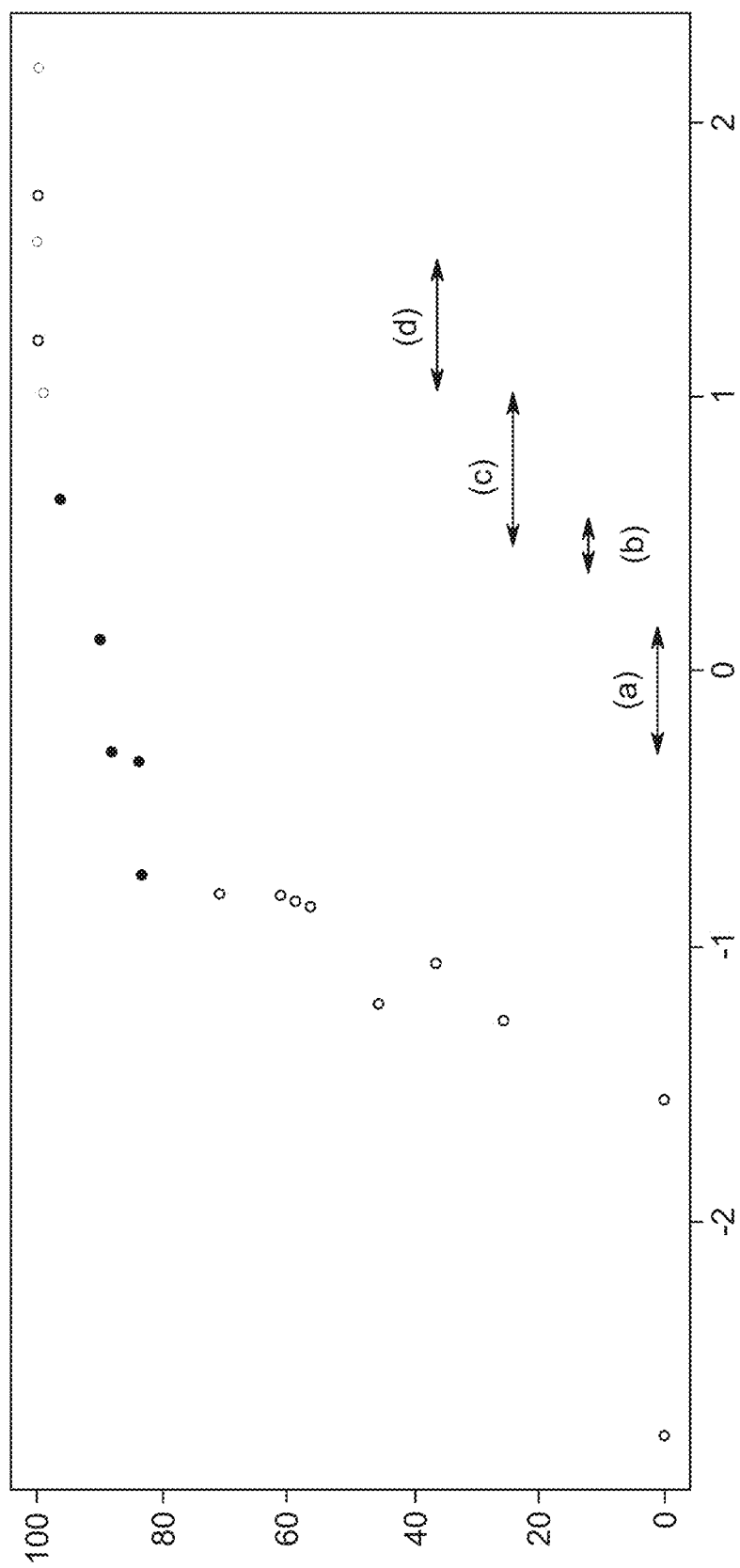
FIG. 5 shows the relationship between plasma concentration and brain HSD1 enzyme occupancy for Compound A. Abscissa: $\log_{10}$(Compound A plasma concentration in ng/mL), ordinate: brain HSD1 enzyme occupancy (%). Intra-graph lines indicate plasma concentration ranges associated with daily doses of (a) 0.2 mg, (b) 0.4 mg, (c) 0.7 mg, and (d) 2.0 mg Compound A at steady state.

The relationship of Compound A plasma concentrations to region of interest size weighted average (ROIswa) HSD-1 occupancy in brain was best described by a direct sigmoidal Emax model (FIG. 5).

| Parameter | Estimate | CVSE* |
|---|---|---|
| Maximum effect, Emax (% HSD-1 occupancy) | 97.6% | 1.53% |
| Plasma concentration when half Emax is achieved, EC50 (ng/mL) | 0.102 | 12.65% |
| Hill coefficient | 1.53 | 18.63% |
| Between subject variability on EC50 (variance) | 0.0406 | |
| Additive residual variability (% HSD-1 occupancy) | 4.70 | |

*NONMEM-provided standard error of the estimate as percent coefficient of variation.

Figure 6A:
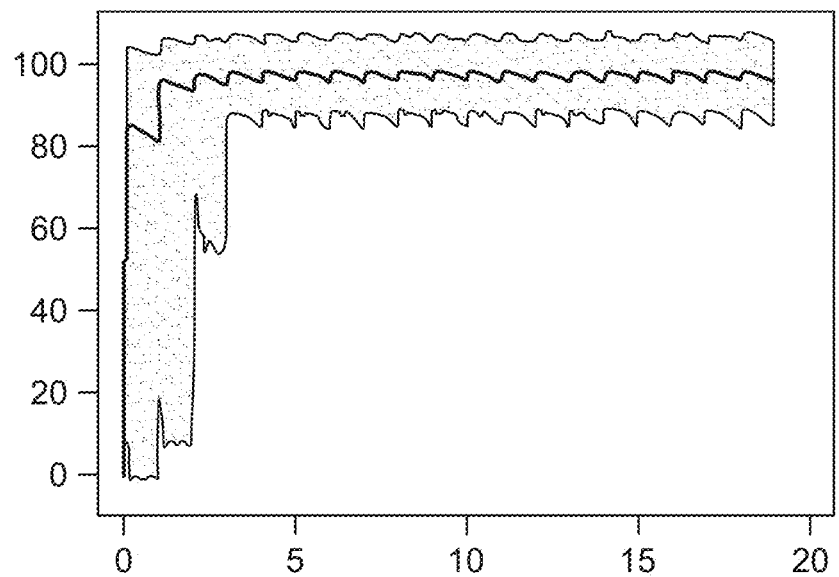
FIG. 6 shows simulations of HSD1 inhibition for patients by Compound A. 3 mg first dose, then daily doses of (a) 1 mg QD; (b) 0.1 mg QD. The abscissa is labeled as days of dose administration.
Figure 6B:
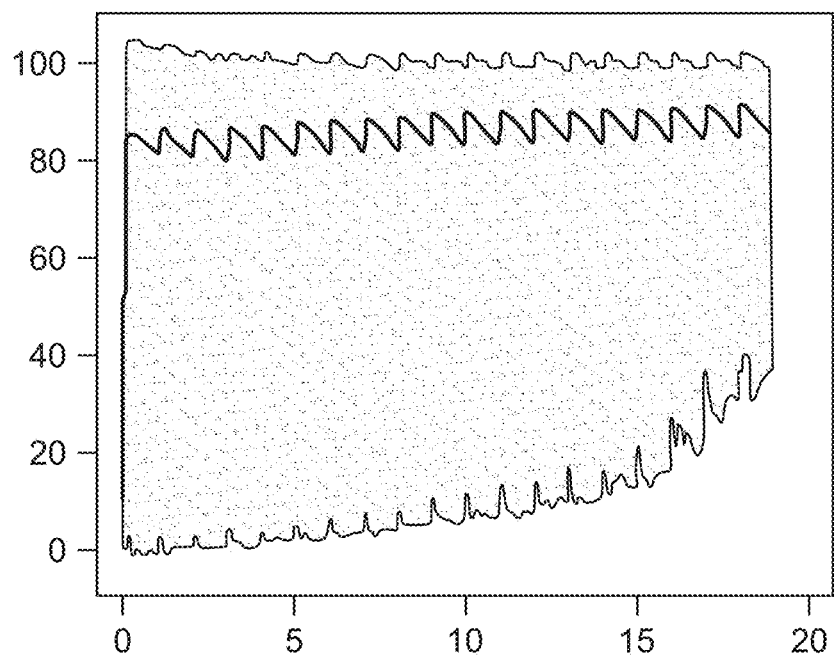
Figure 7A:
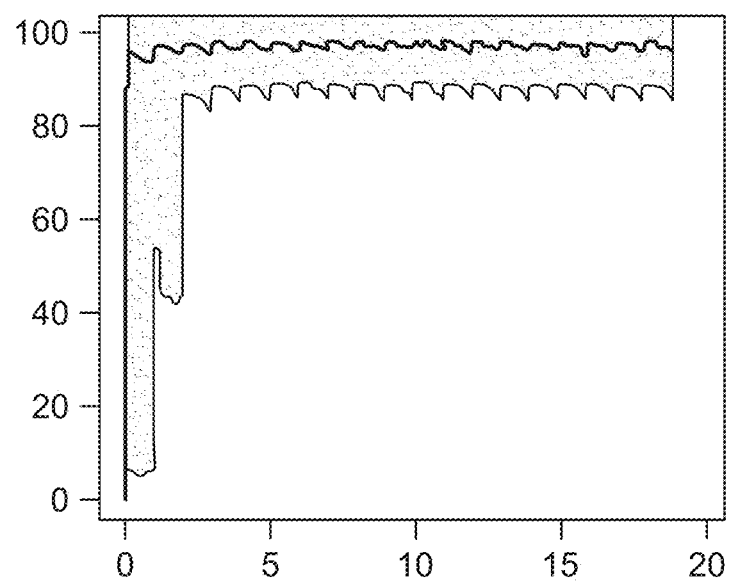
FIG. 7 shows simulations of HSD1 inhibition for patients by Compound A. 4 mg first dose, then daily doses of (a) 1 mg QD; (b) 0.1 mg QD. The abscissa is labeled as days of dose administration.
Figure 7B:
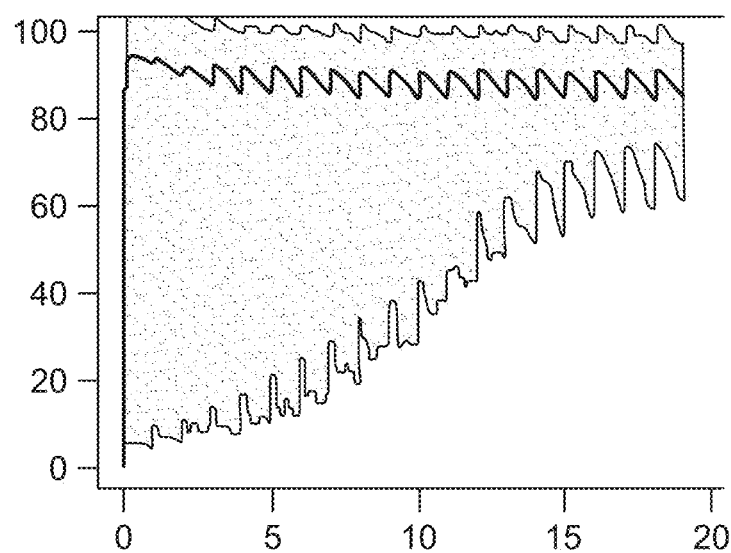
Figure 8:
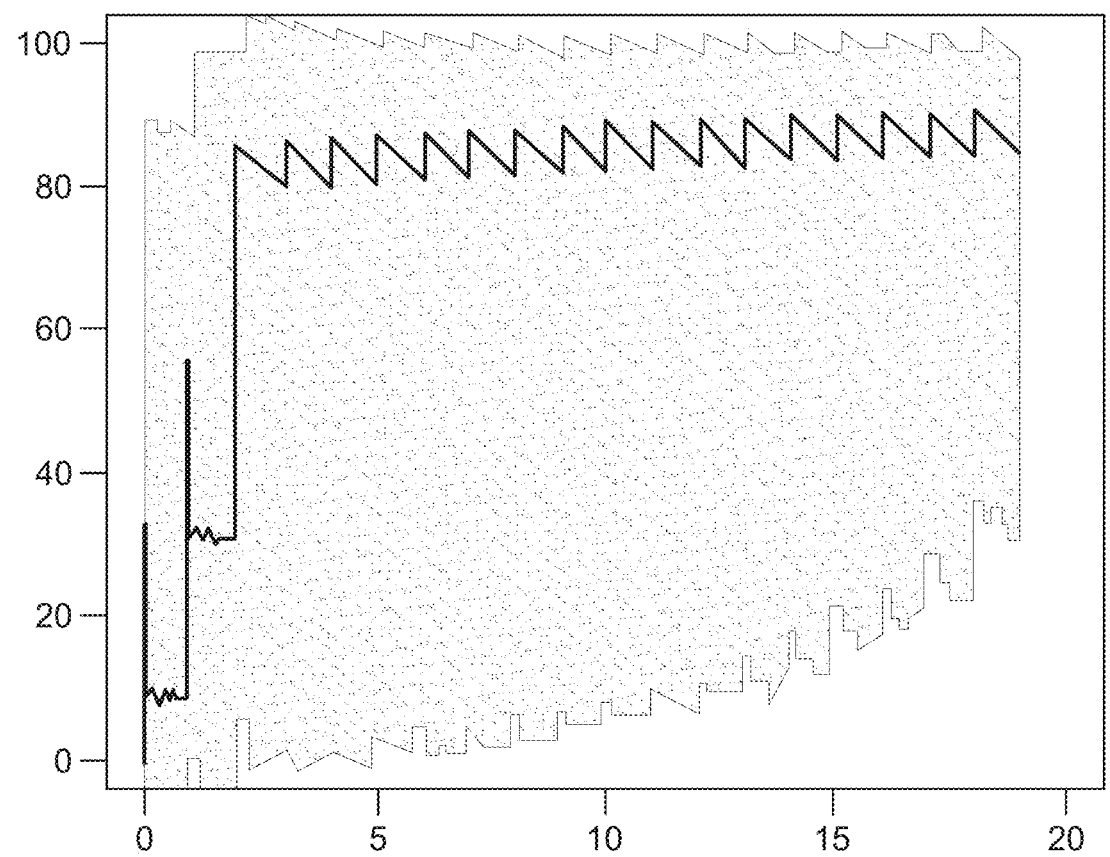
FIG. 8 shows simulations of HSD1 inhibition for patients by Compound A. Three 1 mg daily doses, then daily doses of 0.1 mg QD. The abscissa is labeled as days of dose administration.

The population pharmacokinetic model of Example 1 was used to simulate brain HSD-1 occupancy following single and multiple doses of SPI-62. Results are shown in FIG. 6 (3 mg initial dose, then (a) 1 mg QD; (b) 0.1 mg QD), FIG. 7 (4 mg initial dose, then (a) 1 mg QD; (b) 0.1 mg QD), and FIG. 8 (3×1 mg initial doses, then 0.1 mg QD).

Example 5: Effects of Compound a on Central Metabolism in Diabetic Patients

Adults with painful diabetic peripheral neuropathy were randomized to treatment with SPI-62, placebo for SPI-62, or pregabalin (positive control) for 6 weeks. An interim review of trial results after 150 subjects completed treatment showed that pain relief was not any better with Compound A compared to the placebo group. The trial was terminated. Descriptive analysis on parameters of glycemic control, blood lipids, blood pressure, and weight was conducted. Favorable numeric trends for Compound A compared to placebo were observed on glycated hemoglobin (HbAlc), plasma glucose, urine glucose, cholesterol, and triglycerides, but not on systolic or diastolic blood pressure or weight. As this was an exploratory analysis, statistical hypothesis tests were not performed. The results suggest that larger effect sizes of Compound A on glycemic control and blood lipids might be observed when such parameters are influenced directly by corticosteroid medication. The results do not rule out possibility of an effect of Compound A on blood pressure and weight when such parameters are influenced directly by corticosteroid medication or during longer duration of therapy.

| Parameter | Placebo | SPI-62 |
|---|---|---|
| HbA1c (%) | 0.20 ± 0.21 | −0.31 ± 0.11 |
| Plasma glucose (mM) | 1.67 ± 0.75 | 0.084 ± 0.38 |
| Urine glucose (% positive) | 16.4 ± 7.7 | −2.5 ± 3.0 |
| Cholesterol (mM) | 0.28 ± 0.12 | −0.48 ± 0.12 |
| Triglycerides (mM) | 0.30 ± 0.24 | −0.11 ± 0.09 |
| Systolic BP (mm Hg) | −3 ± 3 | −1 ± 3 |
| Diastolic BP (mm Hg) | −1 ± 1 | 0 ± 2 |
| Weight (kg) | −0.4 ± 0.4 | −0.3 ± 0.3 |

Example 6: Blockade of Corticosteroid Adverse Effects by Compound A

Figure 9:
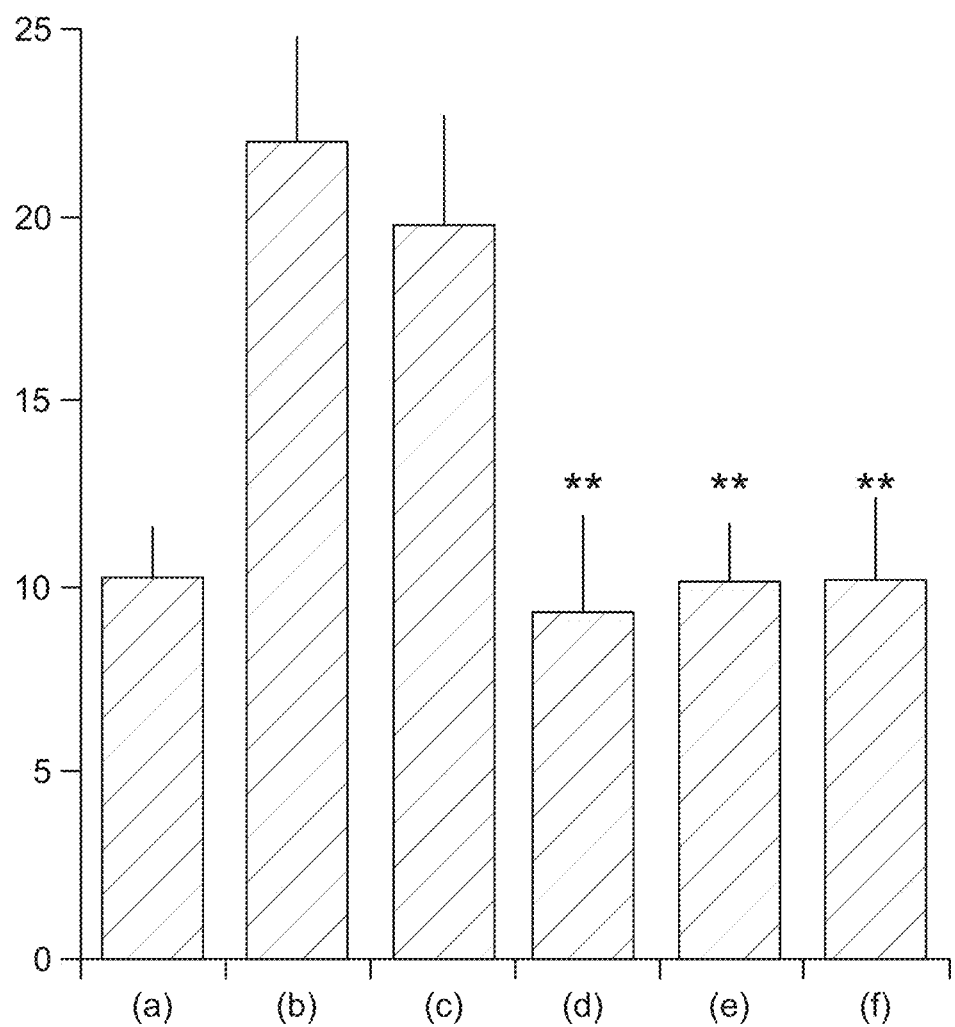
FIG. 9 shows reversal of CS-induced tail biting behavior by Compound A. Vertical axis: tail biting, sec. **$P$, 0.01 vs. 0 dose. (a) no CS; (b)-(f) CS; dosage of Compound A (mg/kg): (b) 0; (c) 0.01; (d) 0.03; (e) 1; (f) 3.

Increased tail biting, an anxiety behavior, was induced in magnesium-deficient mice with administration of N-methyl-D-aspartate and corticosterone (CS). Tail biting was not induced by N-methyl-D-aspartate without co-administration of CS (FIG. 9(a)). Single doses of 0.3 to 3 mg/kg SPI-62 fully reversed the CS-dependent increase of tail biting behavior (FIG. 9(d)-(f)).

Mice typically prefer to explore the novel arm of a Y-maze, a behavior considered indicative of short-term memory. Corticosterone (CS) decreases the percentage of times mice enter the novel arm of a Y maze, and so is considered to have a negative cognitive effect. Single doses of 0.3 to 3 mg/kg Compound A (FIG. 10(d)-(f) restored a more normal behavior pattern.

Example 7: Dose Scenarios in Clinical Practice

In a patient for whom chronic corticosteroid prescription is indicated, it would be desired to achieve full HSD-1 inhibition within a finite number of days of HSD-1 inhibitor administration. For example, dose levels of 0.4, 0.7, and 2 mg of Compound A have been observed to achieve full HSD-1 inhibition after 9 to 11, 5 to 6, and 2 doses. As well, a dose level of 1 mg of Compound A could be expected to achieve full HSD-1 inhibition after 3 to 4 doses. Such patients would most commonly be prescribed oral corticosteroids but also might be prescribed corticosteroid medications by other administration routes that result in systemic corticosteroid exposure such as inhaled, intranasal, topical, or intramuscular.

In a patient for whom sub-chronic corticosteroid prescription is indicated, it would be desired to achieve full HSD-1 inhibition concurrently with the first corticosteroid dose. For example, an initial dose of more than 4 mg of Compound A (e.g., 6 mg), followed by daily doses of more than 0.1 mg of Compound A (e.g., 0.2 to 2 mg), could be selected.

In a patient for whom a specific six-day corticosteroid prescription is indicated, wherein the patient is instructed to take 6, 5, 4, 3, 2, and 1 equivalent corticosteroid dosage forms on the $1^{st}$, $2^{nd}$, $3^{rd}$, $4^{th}$, $5^{th}$, and $6^{th}$ days, full HSD-1 inhibition throughout the course of treatment could be achieved by a fixed dose combination of a corticosteroid with an amount (N) of a HSD-1 inhibitor wherein 6N is sufficient to achieve full HSD-1 inhibition concurrently with the first corticosteroid dose. For example, a fixed dose combination such that the amount of Compound A in six dosage forms is more than 4 mg (e.g., 0.7 to 1 mg) could be selected.

In a patient for whom acute corticosteroid prescription is indicated, it would be desired to achieve full HSD-1 inhibition concurrently with the corticosteroid dose and maintain substantial HSD-1 inhibition through the duration of substantial pharmacologic effect of the corticosteroid dose. Such patients would most commonly be prescribed intramuscular, intralesional, or intravenous corticosteroids. For example, an intramuscular dose of 40 to 240 mg methylprednisolone or an intralesional dose of 20 to 160 mg methylprednisolone can be expected to have substantial pharmacologic effect for at least 5 to 10 days. A single oral dose of more than 4 mg of Compound A (e.g., 6 mg) could be expected to rapidly achieve full HSD-1 inhibition and maintain substantial HSD-1 inhibition for at least 5 to 10 days.

Example 8: Dosage Formulation for Tablets with 1 mg Compound A

The table below provides a tablet dosage for 1 mg of Compound A.

| Component | Function | Reference to Standard | Quantity (mg per tablet) |
|---|---|---|---|
| Compound A | Active ingredient | In house | 1.0 |
| Hypromellose | Filler | JP | 1.0 |
| D-Mannitol | Filler | JP | 100.7 |
| Croscarmellose sodium | Disintegrant | JP | 26.0 |
| Magnesium stearate | Lubricant | JP | 1.3 |
| Subtotal | | | 130.0 |
| Opadry ® 03F42203 | Coating agent | In house | 3.9 |
| Purified water | Processing agent | JP | 1 |
| Total | | | 133.9 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for administering a corticosteroid to a patient in need thereof, comprising:
   determining a target threshold of 0.2 for the ratio of urinary (tetrahydrocortisol+allotetrahydrocortisol) to urinary tetrahydrocortisone for the patient; and
   administering a HSD-1 inhibitor to a patient who is being administered a corticosteroid,
wherein:
   the corticosteroid is not prednisone;
   the HSD-1 inhibitor is 4-{5-[1-(4-chloro-2,6-difluorophenoxy)-1-methylethyl]-4-methyl-4H-1,2,4-triazol-3-yl-3-fluorobenzamide or a pharmaceutically acceptable salt thereof (Compound A); and
   the HSD-1 inhibitor is administered at a first dose for a first time period, such that the administration is effective to maintain or reduce the patient's urinary ratio of urinary (tetrahydrocortisol+allotetrahydrocortisol) to urinary tetrahydrocortisone at a level below the target threshold.

2. The method of claim 1, wherein administering the corticosteroid reduces or prevents-side effects associated with corticosteroid administration in the patient.

3. The method of claim 2, wherein the administration is effective to reduce the patient's urinary ratio of urinary (tetrahydrocortisol+allotetrahydrocortisol) to urinary tetrahydrocortisone at a level below the target threshold within 1 day, or within 2 to 7 days.

4. The method of claim 1, wherein the patient is administered the corticosteroid at a first dose for a first time period.

5. The method of claim 4, further comprising administering a second dose of the corticosteroid to the patient, or a second dose of the HSD-1 inhibitor.

6. The method of claim 5, wherein the second dose of the corticosteroid is a different amount than the first dose, or is the same amount as the first dose.

7. The method of claim 1, wherein a second dose of the HSD-1 inhibitor is not administered to the patient.

8. The method of claim 1, wherein the first dose of the HSD-1 inhibitor is 0.2 mg, 0.7 mg, 1 mg, 2 mg, 3 mg, 4 mg, 5 mg, or 6 mg.

9. The method of claim 5, further comprising administering a second dose of the HSD-1 inhibitor.

10. The method of claim 9, wherein prior to administering the second dose of the HSD-1 inhibitor, the method further comprises measuring the ratio of urinary (tetrahydrocortisol+allotetrahydrocortisol) to urinary tetrahydrocortisone for the patient.

11. The method of claim 10, further comprising adjusting the dose of HSD-1 inhibitor to maintain or reduce the patient's ratio of urinary (tetrahydrocortisol+allotetrahydrocortisol) to urinary tetrahydrocortisone at a level below the target threshold.

12. The method of claim 9, wherein the second dose of the HSD-1 inhibitor is the same as the first dose of the HSD-1 inhibitor; or the second dose of the HSD-1 inhibitor is more than the first dose of the HSD-1 inhibitor; or the second dose of the HSD-1 inhibitor is less than the first dose of the HSD-1 inhibitor.

13. The method of claim 1, wherein the corticosteroid is administered orally; or the corticosteroid is administered intravenously or intramuscularly.

14. The method of claim 1, wherein the HSD-1 inhibitor is administered orally; or the HSD-1 inhibitor is administered intravenously.

15. The method of claim 1, wherein the corticosteroid is administered to treat a chronic disease or disorder; or the corticosteroid is administered to treat an acute disease or disorder.

16. The method of claim 1, wherein the corticosteroid is chosen from alclometasone, amcinonide, beclometasone, betamethasone, budesonide, ciclesonide, clobetasol, clocortolone, cloprednol, cortivazol, deflazacort, desonide, desoximetasone, dexamethasone, diflorasone, diflucortolone, difluprednate, fludrocortisone, fludroxycortide, flumetasone, flunisolide, fluocinolone, fluocinonide, fluocortin, fluocortolone, fluorometholone, fluperolone, fluticasone, fluprednidene, formocortal, halcinonide, halometasone, hydrocortisone, loteprednol, medrysone, methylprednisolone, mometasone, paramethasone, prednicarbate, prednisolone, prednylidene, rimexolone, tixocortol, triamcinolone, ulobetasol, combinations thereof, pharmaceutically acceptable salts thereof, or esters thereof.

17. The method of claim 16, wherein the corticosteroid is betamethasone or a pharmaceutically acceptable salt or ester thereof, and is administered at a dose of from about 0.5 to 20 mg; or
   wherein the corticosteroid is prednisolone or a pharmaceutically acceptable salt or ester thereof, and is administered at a dose of from about 0.5 to 200 mg; or
   wherein the corticosteroid is dexamethasone or a pharmaceutically acceptable salt or ester thereof, and is administered at a dose of from about 0.1 to 40 mg; or
   wherein the corticosteroid is budesonide or a pharmaceutically acceptable salt or ester thereof, and is administered at a dose of from 0.25 mg to 9 mg; or
   wherein the corticosteroid is hydrocortisone or a pharmaceutically acceptable salt or ester thereof, and is administered at a dose of from about 20 to 800 mg; or
   wherein the corticosteroid is deflazacort or a pharmaceutically acceptable salt or ester thereof, and is administered at a dose of from about 0.25 mg to 1 mg/kg/day; or
   wherein the corticosteroid is methylprednisolone or a pharmaceutically acceptable salt or ester thereof, and is administered orally at a dose of from 0.4 to about 240 mg; or
   wherein the corticosteroid is methylprednisolone or a pharmaceutically acceptable salt or ester thereof, and is administered intravenously at a dose of from 10 to about 40 mg.

18. The method of claim 1, wherein the corticosteroid is administered to treat a disease or disorder chosen from:
   endocrine disorders, primary or secondary adrenocortical insufficiency, congenital adrenal hyperplasia, nonsuppurative thyroiditis, and hypercalcemia associated with cancer;
   rheumatic disorders, adjunctive therapy for short-term administration (to tide the patient over an acute episode or exacerbation) in psoriatic arthritis, rheumatoid arthritis, ankylosing spondylitis, acute and subacute bursitis, acute nonspecific tenosynovitis, acute gouty arthritis, post-traumatic osteoarthritis, synovitis of osteoarthritis, acute rheumatic carditis, dermatomyositis, temporal arteritis, polymyositis, and systemic lupus erythematosus and epicondylitis;
   collagen diseases, collagen diseases during an exacerbation or as maintenance therapy in selected cases of systemic lupus erythematosus, systemic dermatomyositis (polymyositis), and acute rheumatic carditis;
   dermatologic diseases, pemphigus, bullous dermatitis herpetiformis, severe erythema multiforme (Stevens-Johnson syndrome), exfoliative dermatitis, exfoliative erythroderma, mycosis fungoides, severe psoriasis, and severe seborrheic dermatitis;

intractable to adequate trials of conventional treatment, seasonal or perennial intractable to adequate trials of conventional treatment such as seasonal or perennial allergic rhinitis, bronchial asthma, contact dermatitis, atopic dermatitis, serum sickness, transfusion reactions, and drug hypersensitivity reactions;

ophthalmic diseases, severe acute and chronic allergic and inflammatory processes involving the eye and its adnexa, allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis, ocular inflammatory conditions unresponsive to topical corticosteroids, and iridocyclitis;

respiratory diseases, symptomatic sarcoidosis, Loeffler's syndrome not manageable by other means, berylliosis, fulminating or disseminated pulmonary tuberculosis when used concurrently with appropriate antituberculous chemotherapy, idiopathic eosinophilic pneumonias, symptomatic sarcoidosis, and aspiration pneumonitis;

hematologic disorders, idiopathic thrombocytopenia purpura in adults, secondary thrombocytopenia in adults, acquired (autoimmune) hemolytic anemia, erythroblastopenia (RBC anemia), pure red cell aplasia, and congenital (erythroid) hypoplastic anemia;

neoplastic diseases, neoplastic diseases for palliative management of leukemias and lymphomas in adults and acute leukemia of childhood;

edematous states, edematous states to induce a diuresis or remission of proteinuria in the nephrotic syndrome, without uremia, of the idiopathic type or that due to lupus erythematosus;

gastrointestinal diseases, gastrointestinal diseases to tide the patient over a critical period of the disease in: ulcerative colitis or regional enteritis;

nervous system disorders, acute exacerbations of multiple sclerosis, cerebral edema associated with primary or metastatic brain tumor, or craniotomy;

renal diseases, renal diseases to induce diuresis or remission of proteinuria in idiopathic nephrotic syndrome or that due to lupus erythematosus; and other diseases or disorders such as tuberculous meningitis with subarachnoid block or, impending block when used concurrently with appropriate antituberculous chemotherapy, and trichinosis with neurologic or myocardial involvement.

19. The method of claim 1, wherein the corticosteroid is administered to treat vasculitis.

20. The method of claim 19, wherein the corticosteroid is administered to treat a disease or disorder chosen from Behcet's disease, central nervous system vasculitis, cryoglobulinemia, Churg-Strass syndrome, giant cell arteritis, granulomatosis with polyangitis, Henoch-Schönlein purpura, hypersensitivity vasculitis, aortic, microscopic polyangiitis, polyarteritis nodosa, polymalgia rheumatica, rheumatoid vasculitis, Takayasu'arteritis, and urticarial vasculitis.

* * * * *

UNITED STATES PATENT AND TRADEMARK OFFICE
CERTIFICATE OF CORRECTION

PATENT NO. : 12,220,412 B2
APPLICATION NO. : 17/289516
DATED : February 11, 2025
INVENTOR(S) : David A. Katz It is certified that error appears in the above-identified patent and that said Letters Patent is hereby corrected as shown below:

In the Specification

In Column 2, Line 2, delete "(ii);" and insert -- (ii) --, therefor.

In Column 4, Line 23, delete "3-yl-3-fluorobenzamide," and insert -- 3-yl}-3-fluorobenzamide, --, therefor.

In Column 7, Lines 33-34, delete "3-yl-3-fluorobenzamide" and insert -- 3-yl}-3-fluorobenzamide --, therefor.

In Column 7, Lines 55-56, delete "3-yl-3-fluorobenzamide" and insert -- 3-yl}-3-fluorobenzamide --, therefor.

In Column 8, Lines 11-12, delete "3-yl-3-fluorobenzamide" and insert -- 3-yl}-3-fluorobenzamide --, therefor.

In Column 8, Lines 36-37, delete "3-yl-3-fluorobenzamide" and insert -- 3-yl}-3-fluorobenzamide --, therefor.

In Column 8, Line 50, delete "3-yl-3-fluorobenzamide" and insert -- 3-yl}-3-fluorobenzamide --, therefor.

In Column 14, Lines 29-30, delete "Stevens-" and insert -- (Stevens- --, therefor.

In Column 15, Line 17, delete "cryogloblinemia," and insert -- cryoglobulinemia, --, therefor.

In Column 17, Line 47, delete "3-yl-3-fluorobenzamide" and insert -- 3-yl}-3-fluorobenzamide --, therefor.

In Column 22, Line 65, delete "(HbAlc)," and insert -- (HbA1c), --, therefor.

Signed and Sealed this
Thirteenth Day of May, 2025

Coke Morgan Stewart
*Acting Director of the United States Patent and Trademark Office*

CERTIFICATE OF CORRECTION (continued)
U.S. Pat. No. 12,220,412 B2

Figure 10:
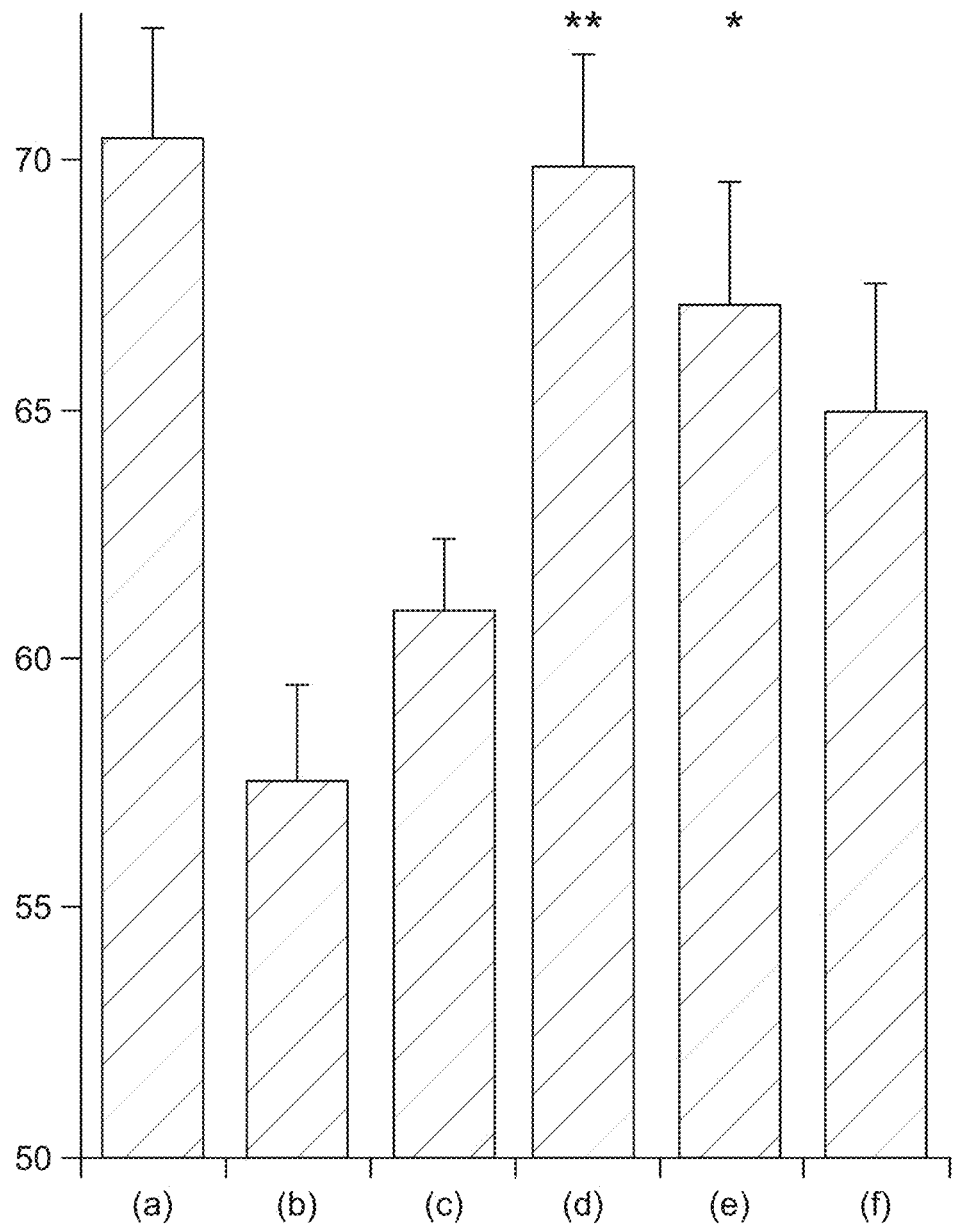
FIG. 10 shows restoration of CS-induced deficit of maze exploration behavior by Compound A. Vertical axis: alternation rate (%). *$P<0.05$; **$P<0.01$ vs 0 dose. (a) no CS; (b)-(f) CS; dosage of Compound A (mg/kg): (b) 0; (c) 0.01; (d) 0.03; (e) 1; (f) 3.

In Column 23, Line 38, delete "(FIG. 10(d)-(f)" and insert -- (FIG. 10(d)-(f)) --, therefor.

In the Claims

In Column 25, Claim 1, Lines 12-13, delete "3-yl-3-fluorobenzamide" and insert -- 3-yl}-3-fluorobenzamide --, therefor.

In Column 26, Claim 17, Line 21, delete "from about" and insert -- from --, therefor.

In Column 26, Claim 17, Line 25, delete "from about" and insert -- from --, therefor.

In Column 26, Claim 17, Line 28, delete "from about" and insert -- from --, therefor.

In Column 26, Claim 17, Line 34, delete "from about" and insert -- from --, therefor.

In Column 26, Claim 17, Line 37, delete "from about" and insert -- from --, therefor.

In Column 26, Claim 17, Line 41, delete "about 240" and insert -- 240 --, therefor.

In Column 26, Claim 17, Line 46, delete "about 40" and insert -- 40 --, therefor.

In Column 27, Claim 18, Line 11, delete "ulcers ," and insert -- ulcers, --, therefor.

In Column 27, Claim 18, Line 25, delete "thrombocytopenia" and insert -- thrombocytopenic --, therefor.

In Column 28, Claim 18, Lines 14-19, delete "erythematosus; and other diseases or disorders such as tuberculous meningitis with subarachnoid block or, impending block when used concurrently with appropriate antituberculous chemotherapy, and trichinosis with neurologic or myocardial involvement." and insert -- erythematosus. --, therefor.

In Column 28, Claim 20, Lines 25-26, delete "cryogloblinemia," and insert -- cryoglobulinemia, --, therefor.

In Column 28, Claim 20, Line 26, delete "Churg-Strass" and insert -- Churg-Strauss --, therefor.

In Column 28, Claim 20, Line 27, delete "polyangitis," and insert -- polyangiitis, --, therefor.

In Column 28, Claim 20, Line 29, delete "polymalgia" and insert -- polymyalgia --, therefor.

In Column 28, Claim 20, Line 30, delete "Takayasu'arteritis," and insert -- Takayasu's arteritis, --, therefor.